United States Patent [19]

Hori et al.

[11] 4,448,963
[45] May 15, 1984

[54] 4-[4-(THIAZOLYL-AMINO)BENZYL]-2,3-DIOXOPIPERAZINE DERIVATIVES, ACID ADDITION SALTS THEREOF AND PROCESS FOR PRODUCING SAME

[75] Inventors: Takako Hori, Toyama; Chosaku Yoshida, Takaoka; Yasuo Kiba, Toyama; Ryuko Takeno, Toyama; Joji Nakano, Toyama; Jun Nitta, Namekawa; Sumiko Kishimoto, Toyama; Shohachi Murakami, Toyama; Hisatsugu Tsuda, Toyama; Isamu Saikawa, Toyama, all of Japan

[73] Assignee: Toyama Chemical Co., Ltd., Tokyo, Japan

[21] Appl. No.: 351,257

[22] Filed: Feb. 22, 1982

Related U.S. Application Data

[62] Division of Ser. No. 169,457, Jul. 16, 1980.

[30] Foreign Application Priority Data

Jul. 24, 1979 [JP] Japan .................................. 54-93234

[51] Int. Cl.³ .................... C07D 241/06; A61K 31/41
[52] U.S. Cl. ...................................... 544/367; 544/55; 544/60; 544/96; 544/121; 544/295; 544/360; 544/366; 544/368; 544/369; 544/370; 544/372; 544/373; 424/248.4; 424/250; 424/251
[58] Field of Search ............... 544/295, 360, 366, 369, 544/379, 367

[56] References Cited

U.S. PATENT DOCUMENTS 4,110,327  8/1979  Saikawa et al. ..................... 544/369

OTHER PUBLICATIONS

Hori et al., Chem. & Pharm. Bulletin, vol. 29, (3), pp. 684-698, (1981).
Hori et al., Chem. & Pharm. Bulletin, vol. 29, (6), pp. 1594-1605, (1981).

*Primary Examiner*—Donald G. Daus
*Assistant Examiner*—S. A. Gibson
*Attorney, Agent, or Firm*—Oblon, Fisher, Spivak, McClelland & Maier

[57] ABSTRACT

A 1-(4-aminobenzyl)-2,3-dioxopiperazine derivative represented by the formula:

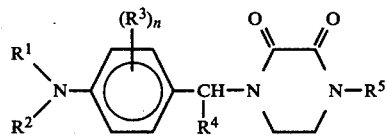

and an acid addition salt thereof have excellent carcinostatic activity but a low toxicity. Therefore, said compounds are useful as medicines and also as intermediates.

2 Claims, No Drawings

4-[4-(THIAZOLYL-AMINO)BENZYL]-2,3-DIOXOPIPERAZINE DERIVATIVES, ACID ADDITION SALTS THEREOF AND PROCESS FOR PRODUCING SAME

This is a division, of application Ser. No. 169,457, filed July 16, 1980.

This invention relates to novel 1-(4-aminobenzyl)-2,3-dioxopiperazine derivatives and acid addition salts thereof, and to a process for producing the same.

The compounds of this invention are per se excellent in carcinostatic activity, low in toxicity, useful as medicines, and useful also as intermediates.

An object of this invention is to provide novel 1-(4-aminobenzyl)-2,3-dioxopiperazine derivatives having 1-(4-aminobenzyl)-2,3-dioxopiperazinyl moiety in their molecules, and acid addition salts thereof.

Another object of this invention is to provide novel 1-(4-aminobenzyl)-2,3-dioxopiperazine derivatives which have a carcinostatic activity and are low in toxicity, and acid addition salts thereof.

A further object of this invention is to provide a process for producing novel 1-(4-aminobenzyl)-2,3-dioxopiperazine derivatives, or acid addition salts thereof.

Other objects and advantages of this invention will be apparent from the following description.

According to this invention, there is provided a novel 1-(4-aminobenzyl)-2,3-dioxopiperazine derivative represented by the formula (I):

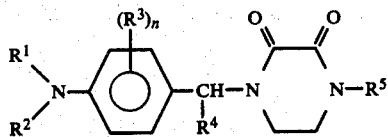

wherein $R^1$ and $R^2$ may be the same or different and independently represent a hydrogen atom or a substituted or unsubstituted alkyl, cycloalkyl, aralkyl, acyl, thiocarbamoyl, alkylthioimidoyl, amidino or heterocyclic group, or $R^1$ and $R^2$, when taken together with the nitrogen atom to which they are attached, may form a substituted or unsubstituted heterocyclic group; n is 0, 1 or 2; $nR^3$'s may be the same or different and independently represent a halogen atom, an amino group, or a substituted or unsubstituted alkyl, alkoxy, alkylamino or dialkylamino group; $R^4$ represents a hydrogen atom or a substituted or unsubstituted alkyl group; and $R^5$ represents a hydrogen atom or a substituted or unsubstituted alkyl, alkenyl, alkadienyl, cycloalkyl, aralkyl, aryl, or heterocyclic group; or an acid addition salt thereof.

In the formula (I), $R^1$ and $R^2$ may be alkyl, preferably $C_{1-8}$alkyl, such as, for example, methyl, ethyl, propyl, isopropyl, butyl, pentyl, hexyl, heptyl, octyl, or the like; cycloalkyl, preferably $C_{5-6}$cycloalkyl, such as, for example, cyclopentyl, cyclohexyl, or the like; aralkyl, preferably ar-$C_{1-4}$alkyl, such as, for example, benzyl, phenethyl, or the like; acyl, preferably $C_{1-4}$alkanoyl, such as, for example, acetyl, propionyl, butyryl, or the like, and aroyl, such as, for example, benzoyl, furoyl, thenoyl, pyridylcarbonyl, or the like; thiocarbamoyl, such as, for example, thiocarbamoyl, phenylthiocarbamoyl, or the like; alkylthioimidoyl, preferably $C_{1-4}$alkylthioimidoyl, such as, for example, methylthioimidoyl, ethylthioimidoyl, or the like; amidino; or heterocyclic, preferably saturated or unsaturated 5- or 6-membered heterocyclic, group containing at least one hetero atom selected from the group consisting of O, S and N or a fused heterocyclic group formed by fusion between a benzene ring and the above-mentioned heterocyclic ring (hereinafter the term "heterocyclic group" means to include said heterocyclic group and said fused heterocyclic group), such as, for example, piperidinyl, 2-pyridyl, 3-pyridyl, 4-pyridyl, 2-pyrimidinyl, 4-pyrimidinyl, 5-pyrimidinyl, 3-pyridazinyl, 4-pyridazinyl, pyrazinyl, triazinyl, 2-pyrrolidinyl, 3-pyrrolidinyl, 3-pyrazolyl, 4-pyrazolyl, 5-pyrazolyl, 4-triazolyl, 5-triazolyl, 5-tetrazolyl, 2-thienyl, 3-thienyl, 2-furyl, 3-furyl, 2-thiazolyl, 4-thiazolyl, 5-thiazolyl, 3-isothiazoyl, 4-isothiazolyl, 5-isothiazolyl, 2-oxozolyl, 4-oxazolyl, 5-oxazolyl, 3-isoxazolyl, 4-isoxazolyl, 5-isoxazolyl, 2-imidazolyl, 4-imidazolyl, 5-imidazolyl, 2-indolyl, 3-indolyl, 5-indolyl, 2-benzimidazolyl, 5-benzimidazolyl, and the like. When $R^1$ and $R^2$ forms a heterocyclic ring together with the nitrogen atoms to which $R^1$ and $R^2$ attach, said heterocyclic ring includes specifically piperidine, piperazine, morpholine, oxopyrrolidine, oxopiperidine, oxopiperazine, aziridine, pyrrolidine, succinylimide, phthalimide, pyrrole, imidazole, pyrazole, tetrazole, imidazoline, thiazoline, isothiazoline, oxazoline, isoxazoline, and the like. The above-mentioned $R^1$ and $R^2$ may be substituted by at least one substituent selected from the group consisting of halogen atoms such as fluorine, chlorine, bromine, and iodine; hydroxyl group; carboxyl group; $C_{1-4}$alkoxycarbonyl groups such as methoxycarbonyl, ethoxycarbonyl, and the like; ar-$C_{1-4}$alkyloxycarbonyl groups such as benzyloxycarbonyl and the like; aryloxycarbonyl groups such as phenoxycarbonyl and the like; $C_{1-4}$alkyl groups such as methyl, ethyl, propyl, isopropyl, butyl or the like; di-$C_{1-4}$alkoxy-$C_{1-4}$alkyl groups such as dimethoxyethyl, diethoxyethyl and the like; $C_{2-4}$alkenyl groups such as vinyl, allyl and the like; ar-$C_{1-4}$alkyl groups such as benzyl, phenethyl and the like; $C_{5-6}$cycloalkyl groups such as cyclopentyl, cyclohexyl, and the like; cyano group, mercapto group; $C_{1-4}$alkylthio groups such as methylthio, ethylthio and the like; nitro group; oxo group; imino group; thioxo group; $C_{1-4}$alkanoylamino group such as acetamido and the like; $C_{1-4}$alkoxy groups such as methoxy, ethoxy, butoxy and the like; ar-$C_{1-4}$alkyloxy group such as benzyloxy and the like; $C_{1-8}$acyl groups such as formyl, acetyl, propionyl, butyryl, benzoyl, and the like; amino group; $C_{1-4}$alkylamino groups such as methylamino, ethylamino, propylamino, and the like; di-$C_{1-4}$alkylamino groups such as dimethylamino, diethylamino, dipropylamino, and the like; arylamino groups such as anilino and the like; ar-$C_{1-4}$alkylamino groups such as benzylamino, dimethylaminobenzylamino, diethylaminobenzylamino, phenethylamino, and the like; the same heterocyclic groups as defined for $R^1$ and $R^2$; heterocyclic amino groups such as pyridylamino, pyrimidinylamino, and the like, etc.

The halogen atom, alkyl group, alkoxy group, alkylamino group and dialkylamino group for $R^3$ and the alkyl group for $R^4$ include the same specific examples mentioned for $R^1$ and $R^2$. $R^3$ and $R^4$ may be substituted by the same substituents as mentioned for $R^1$ and $R^2$.

$R^5$ is an alkyl group, preferably $C_{1-8}$alkyl, such as methyl, ethyl, propyl, butyl, pentyl, hexyl, heptyl, octyl, or the like; an alkenyl group, preferably $C_{2-4}$alkenyl, such as vinyl, allyl, or the like; an alkadienyl group, preferably $C_{4-10}$alkadienyl, such as 1,3-butadienyl, 2,4-hexadienyl, geranyl, or the like; a cycloalkyl group, preferably $C_{5-6}$cycloalkyl, such as cyclopentyl, cyclohexyl, or the like; an aralkyl group, preferably ar-$C_{1-4}$alkyl, such as benzyl, phenethyl, or the like; an aryl group, such as phenyl, naphthyl, or the like; and a heterocyclic group, which includes the same specific examples as mentioned for $R^1$ and $R^2$. $R^5$ may be substituted by at least one substituent selected from the group consisting of the substituents mentioned above for $R^1$ and $R^2$; $C_{1-8}$acyloxy groups such as acetyloxy, propionyloxy, benzoyloxy and the like; ar-$C_{1-4}$alkyloxy groups such as benzyloxy or the like; and $C_{5-6}$cycloalkylamino groups such as cyclopentylamino, cyclohexylamino, and the like. When $R^5$ is substituted by a heterocyclic group, the heterocyclic group may be substituted by the same substituent as mentioned above for $R^1$ and $R^2$.

Among the groups listed above, there are preferred combinations of $R^1$ which is a substituted or unsubstituted heterocyclic group with $R^2$ which is a hydrogen atom or a substituted or unsubstituted alkyl, aralkyl or acyl group. Among these combinations, more preferable are combinations in which $R^2$ is a hydrogen atom and $R^5$ is a substituted or unsubstituted alkyl or aralkyl group. It is preferable that $R^1$ and $R^2$ are the same or different and are independently a hydrogen atom or a substituted or unsubstituted alkyl, cycloalkyl, aralkyl or acyl group, or that when $R^1$ and $R^2$ form a substituted or unsubstituted heterocyclic group together with the nitrogen atom to which they attach, $R^1$ and $R^2$ are the same or different and are independently a hydrogen atom or a substituted or unsubstituted alkyl or acyl group. Further, a combination of $R^4$ which is a hydrogen atom with $R^5$ which is a substituted or unsubstituted alkyl or aralkyl group is preferred.

For the formation of the acid addition salts of the compounds represented by the formula (I), any acids may be used so long as the resulting salts are pharmaceutically acceptable, though salts thereof with inorganic or organic acids such as hydrogen chloride, hydrogen bromide, sulfuric acid, p-toluenesulfonic acid, and the like are particularly preferred. Hydrates of the compounds represented by the formula (I) and hydrates of the acid addition salts of the compounds of the formula (I) are also included in this invention.

The carcinostatic activity and acute toxicity of the representative compounds of this invention are explained below.

A. Antitumor Effect a. MIC value against HeLa S3 cells and Ehrlich cells (microplate method)
Number of cells: $2 \times 10^4$ cells/ml
Culture medium: Eagle's MEM + 20% calf embryonic serum
Culture time: 4 days
Judgement: Giemsa staining

TABLE 1

| Compound No. | Structural Formula | MIC Values HeLa S3 (μg/ml) | Ehrlich (μg/ml) |
|---|---|---|---|
| 1 | (2-pyridyl)-NH-(phenylene)-CH₂-N(imide)N-n-C₆H₁₃ | 0.2 | 0.2 |
| 2 | (2-pyridyl)-NH-(phenylene)-CH₂N(imide)N-CH₂-phenyl | 0.39–0.78 | 0.39–0.78 |
| 3 | O₂N-(pyridyl)-NH-(phenylene)-CH₂-N(imide)N-CH₂-phenyl | 3.13–6.25 | 6.25 |
| 4 | H₂N-(pyridyl)-NH-(phenylene)-CH₂-N(imide)N-CH₂-phenyl | <0.05 | <0.05 |
| 5 | (3-pyridyl)-NH-(phenylene)-CH₂-N(imide)N-n-C₆H₁₃ | 3.13 | 3.13 |
| 6 | (thiazolyl)-NH-(phenylene)-CH₂-N(imide)N-n-C₆H₁₃ | 0.78 | 0.78 |

TABLE 1-continued

| Compound No. | Structural Formula | MIC Values HeLa S₃ (μg/ml) | Ehrlich (μg/ml) |
|---|---|---|---|
| 7 | pyrimidine-NH-C₆H₄-CH₂-N(piperazinedione)N-n-C₆H₁₃ | 0.39–0.78 | 0.39–0.78 |
| 8 | pyrimidine-NH-C₆H₄-CH₂-N(piperazinedione)N-pyrazine | 0.78 | 0.39 |
| 9 | pyrimidine-NH-C₆H₄-CH₂-N(piperazinedione)N-CH₂-pyrazine | 1.56–3.13 | 6.25 |
| 10 | pyrimidine-NH-C₆H₄-CH₂-N(piperazinedione)N-CH₂-pyridine-NH₂ | 1.56–3.13 | 12.5 |
| 11 | pyrimidine-NH-C₆H₄-CH₂-N(piperazinedione)N-CH₂-cyclohexyl | 1.56 | 1.56 |
| 12 | pyrimidine-NH-C₆H₄-CH₂-N(piperazinedione)N-phenyl | 0.78 | 0.78 |
| 13 | pyrimidine-NH-C₆H₄-CH₂-N(piperazinedione)N-CH₂-phenyl | 0.1 | 0.1 |
| 14 | pyrimidine-NH-C₆H₄-CH₂-N(piperazinedione)N-(CH₂)₂-phenyl | 0.39 | 0.39 |
| 15 | pyrimidine-NH-C₆H₄-CH₂-N(piperazinedione)N-(CH₂)₃-phenyl | 1.56 | 1.56 |
| 16 | pyrimidine-NH-C₆H₄-CH₂-N(piperazinedione)N-CH₂-C₆H₄-Cl | 1.56 | 1.56 |

TABLE 1-continued

| Compound No. | Structural Formula | MIC Values HeLa S₃ (μg/ml) | Ehrlich (μg/ml) |
|---|---|---|---|
| 17 | pyrimidin-2-yl-NH–C₆H₄–CH₂–N(piperazine-2,3-dione)–N–CH₂–C₆H₄–COOCH₃ | 6.25 | 6.25 |
| 18 | pyrimidin-2-yl-NH–C₆H₄–CH₂–N(piperazine-2,3-dione)–N–CH(CH₃)–C₆H₅ | 3.13 | 6.25 |
| 19 | pyrazin-2-yl-NH–C₆H₄–CH₂–N(piperazine-2,3-dione)–N–n-C₆H₁₃ | 1.56 | 1.56 |
| 20 | pyrazin-2-yl-NH–C₆H₄–CH₂–N(piperazine-2,3-dione)–N–CH₂–C₆H₅ | 0.78 | 1.56 |
| 21 | pyrazin-2-yl-NH–C₆H₄–CH₂–N(piperazine-2,3-dione)–N–n-C₆H₁₃ | 1.56 | 1.56 |
| 22 | pyrimidin-2-yl-NH–C₆H₄–CH(CH₃)–N(piperazine-2,3-dione)–N–CH₂–C₆H₅ | 3.13–6.25 | 6.25 |
| 23 | pyrimidin-2-yl-NH–C₆H₄–CH₂–N(piperazine-2,3-dione)–N–CH₂–C₆H₄–NH-pyrimidin-2-yl | 6.25 | 6.25 |
| 24 | pyridin-2-yl-NH–C₆H₄–CH₂–N(piperazine-2,3-dione)–N–CH₂–C₆H₄–NH-pyridin-2-yl | 3.13 | 3.13 |
| 25 | 5-CH₃-pyridin-2-yl-NH–C₆H₄–CH₂–N(piperazine-2,3-dione)–N–CH₂–C₆H₅ | 0.39 | 0.39 |
| 26 | (C₂H₅)₂N–C₆H₄–CH₂–N(piperazine-2,3-dione)–N–n-C₆H₁₃·HCl | 3.13 | 3.13 |

TABLE 1-continued

| Compound No. | Structural Formula | MIC Values HeLa S₃ ($\mu$g/ml) | Ehrlich ($\mu$g/ml) |
|---|---|---|---|
| 27 | (C₂H₅)₂N–C₆H₄–CH₂–N(piperazinedione)N–CH₂–CH=CH–CH=CHCH₃ | 6.25 | 6.25 |
| 28 | 3-Cl, 4-(C₂H₅)₂N–C₆H₃–CH₂–N(piperazinedione)N–n-C₆H₁₃ | 12.5 | 12.5 |
| 29 | 3-CH₃, 4-(C₂H₅)₂N–C₆H₃–CH₂–N(piperazinedione)N–n-C₆H₁₃ | 12.5 | 12.5 |
| 30 | 3-Cl, 4-(C₂H₅)₂N–C₆H₃–CH₂–N(piperazinedione)N–n-C₆H₁₃·HCl | 3.13 | 3.13 |
| 31 | 4-(piperidino)–C₆H₄–CH₂–N(piperazinedione)N–n-C₆H₁₃·HCl | 3.13 | 3.13 |
| 32 | 4-(C₂H₅NH)–C₆H₄–CH₂–N(piperazinedione)N–n-C₆H₁₃ | 6.25 | 6.25 |
| 33 | 4-((CH₃)₂CHNH)–C₆H₄–CH₂–N(piperazinedione)N–n-C₆H₁₃ | 0.78 | 0.78 |
| 34 | 4-(ClCH₂CONH)–C₆H₄–CH₂–N(piperazinedione)N–n-C₆H₁₃ | 0.39 | 0.39 |
| 35 | 4-(4-pyridyl-CH₂NH)–C₆H₄–CH₂–N(piperazinedione)N–n-C₆H₁₃·2HCl·H₂O | 6.25 | 6.25 |
| 36 | 4-(C₂H₅)₂N–C₆H₄–CH₂–N(piperazinedione)N–CH₂–(4,6-dichloropyrimidin-5-yl) | 12.5 | 12.5 |

TABLE 1-continued

| Compound No. | Structural Formula | MIC Values HeLa S₃ (μg/ml) | Ehrlich (μg/ml) |
|---|---|---|---|
| 37 | (C₂H₅)₂N—⟨phenyl⟩—CH₂—N⟨piperazinedione⟩N—CH₂CH₂NH₂·2HCl | 25 | 25 |
| 38 | (C₂H₅)₂N—⟨phenyl⟩—CH₂—N⟨piperazinedione⟩N—CH₂—⟨pyridyl⟩ | 25 | 25 |
| 39 | (C₂H₅)₂N—⟨phenyl⟩—CH₂—N⟨piperazinedione⟩N—CH₂—⟨pyridyl⟩ | 25 | 25 |
| 40 | (C₂H₅)₂N—⟨phenyl⟩—CH₂—N⟨piperazinedione⟩N—CH₂CH₂NHCH₂—⟨phenyl⟩—N(C₂H₅)₂·3HCl | 12.5 | 12.5 |
| 41 | H₂N, Cl-substituted pyridyl—NH—⟨phenyl⟩—CH₂—N⟨piperazinedione⟩N—CH₂—⟨phenyl⟩ | <0.05 | <0.05 |
| 42 | H₂N, H₃C-substituted pyridyl—NH—⟨phenyl⟩—CH₂—N⟨piperazinedione⟩N—CH₂—⟨phenyl⟩ | <0.05 | <0.05 |
| 43 | H₂N, CH₃-substituted pyridyl—NH—⟨phenyl⟩—CH₂—N⟨piperazinedione⟩N—CH₂—⟨phenyl⟩ | <0.05 | <0.05 |
| 44 | H₂N, CH₃, H₃C-substituted pyridyl—NH—⟨phenyl⟩—CH₂—N⟨piperazinedione⟩N—CH₂—⟨phenyl⟩ | 0.78 | 0.78 |
| 45 | H₂N-pyrimidinyl—NH—⟨phenyl⟩—CH₂—N⟨piperazinedione⟩N—CH₂—⟨phenyl⟩ | 0.05 | 0.05 | b. Effect on Ehrlich Carcinoma (i) Ehrlich ascites carcinoma cells ($1 \times 10^6$ cells/head) were inoculated intraperitoneally into ICR-strain mice (female, 6 to 7 weeks old, each group consisting of 5 or 4 mice), and after 24 hours, the intraperitoneal administration of a test drug was started and effected once a day for 7 days. The effect thereof was judged from the mean survival days.

The test drugs were used in the form of a solution or suspension in a saline solution or a 0.3% carboxymethyl cellulose-containing saline solution.

$$T/C = \frac{\text{Mean survival days in group to which test drug was administered}}{\text{Mean survival days in untreated group}} \times 100 \, (\%)$$

TABLE 2

| Compound No. | Dose (mg/kg) | T/C (%) |
|---|---|---|
| 1 | 200 | >221.4 |
| 2 | 100 | >191.9 |
| 7 | 50 | >186.7 |
|   | 100 | >206.7 |
| 13 | 100 | >176.7 |
| 14 | 100 | >178.7 |
| 23 | 100 | 159 |
| 26 | 40 | 157 |
| 28 | 40 | >173 |
|   | 100 | 165 |
| 29 | 100 | 184 |
| 30 | 100 | 152.1 |
| 34 | 100 | >142.0 |
|   | 200 | 156.8 |
| 35 | 50 | 145.6 |
|   | 100 | >186.7 |
| 36 | 40 | >190 |
|   | 100 | 204 |
| 38 | 100 | 159.5 |
| 39 | 100 | >164.5 |
| 40 | 30 | 153.5 |
| 41 | 50* | 195 |
| 42 | 50 | 149 |

Note:
*Administered once a day for 4 days.

(ii) Ehrlich ascites carcinoma cells (4×10⁶ cells/head) were inoculated subcutaneously at the inguinal region into ICR-strain mice (female, 6 to 7 weeks old, each group consisting of 5 or 4 mice), and after 24 hours, the intraperitaneal or oral administration of a test drug was started and effected once a day for 5 days. The effect thereof was judged from the mean weight of tumor on the 13th or 15th day, respectively.

The test drug was used in the form of a solution or suspension in a saline solution or a 0.3% carboxymethyl cellulose-containing saline solution.

$$T/C = \frac{\text{Mean weight of tumor in group to which test drug was administered}}{\text{Mean weight of tumor in untreated group}} \times 100 \, (\%)$$

TABLE 3

| Compound No. | Administration Route | Dose (mg/kg) | T/C (%) | Judgement Period (days) |
|---|---|---|---|---|
| 4 | Orally | 250 | 56.9 | 15 |
| 13 | Orally | 250 | 32.4 | 15 |
| 26 | Intraperitoneally | 25 | 61 | 13 |
|   |   | 12.5 | 67 | 13 |
|   |   | 6.25 | 64 | 13 |
| 37 | Intraperitoneally | 100 | 65 | 13 |
|   |   | 50 | 52 | 13 |
|   |   | 25 | 54 | 13 |

(iii) Ehrlich ascites carcinoma cells (4×10⁶ cells/head) were inoculated subcutaneously at the right armpit region into ICR-strain mice (female, 7 weeks old, each group consisting of 6 or 7 mice), and after 24 hours, the oral administration or subcutaneous administration at the dorsal region of a test drug was started, and effected once a day for 7 days. The effect thereof was judged from the mean weight of the tumor on the 14th day. The test drug was used in the form of a solution or suspension in a saline solution or a 0.3% carboxymethyl cellulose-containing saline solution.

T/C was calculated in the same manner as in above (ii).

TABLE 4

| Compound No. | Administration Route | Dose (mg/kg) | T/C (%) |
|---|---|---|---|
| 4 | Orally | 50 | 82 |
|   |   | 100 | 65 |
|   | Subcutaneously | 50 | 15 |
| 13 | Orally | 100 | 48 |
|   |   | 200 | 26 |
|   | Subcutaneously | 50 | 54 |
| 41 | Orally | 50 | 78 |
|   | Subcutanelously | 50 | 54 |
| 42 | Orally | 100 | 54 | c. Effect on Sarcoma 180 Carcinoma

Sarcoma 180 ascites cells (1×10⁶ cells/head) were inoculated intraperitoneally into ICR-strain mice (female, 6 weeks old, each group consisting of 4 or 5 mice), and after 24 hours, the intraperitoneal administration of a test drug was started, and effected once a day for 7 days. The effect thereof was judged from the mean survival days. The test drug was used in the form of a solution or suspension in a saline solution or a 0.3% carboxymethyl cellulose-containing saline solution.

$$T/C = \frac{\text{Mean survival days in group to which test drug was administered}}{\text{Mean survival days in untreated group}} \times 100 \, (\%)$$

TABLE 5

| Compound No. | Dose (mg/kg) | T/C (%) | Survival Ratio in Days Shown in Parenthesis | |
|---|---|---|---|---|
| 1 | 200 | >151.6 | 2/4 | (35) |
| 4 | 10 | >221 | 4/5 | (32) |
|   | 20 | >221 | 4/5 | (32) |
| 7 | 100 | >183.1 | 3/4 | (35) |
| 13 | 50 | >204 | 4/5 | (32) |
| 41 | 10 | >193 | 1/5 | (32) |
|   | 20 | >218 | 4/5 | (32) | d. Effect on L-1210 Leukemia (i) L-1210 ascites cells (1×10⁵ cells/head) were inoculated intraperitoneally into BDF₁-strain mice (female, 6 weeks old, each group consisting of 4 mice), and after 24 hours, the intraperitoneal administration of a test drug was started and effected once a day. The effect thereof was judged from the mean survival days. The test drug was used in the form of a solution or suspension in a saline solution or a 0.3% carboxymethyl cellulose-containing saline solution.

T/C was calculated in the same manner as in above b (i).

TABLE 6

| Compound No. | Dose (mg/kg) | Number of Administrations | T/C (%) |
|---|---|---|---|
| 4 | 100 | 3 | 161.9 |
|   | 50 | 9 | 164.3 |
| 7 | 200 | 3 | 159.5 |
|   | 100 | 7 | 168.7 |
|   | 50 | 9 | 181 |
| 13 | 200 | 3 | 229 |
|   | 100 | 6 | 150 |

TABLE 6-continued

| Compound No. | Dose (mg/kg) | Number of Administrations | T/C (%) |
|---|---|---|---|
|  | 50 | 9 | 240.5 |
| 41 | 20 | 7 | 236 |
| 42 | 50 | 7 | 148 |
| 43 | 50 | 7 | 143 |
| 44 | 50 | 3 | 137 |

(ii) L-1210 ascites cells ($1 \times 10^6$ cells/head) were inoculated subcutaneously into BDF$_1$-strain mice (male, 6 weeks old, each group consisting of 4 mice), and after 24 hours, the oral administration of a test drug was started, and effected once a day for 7 hours. The effect thereof was judged from the mean survival days and the weight of the tumor on the 9th day.

The test drug was used in the form of a suspension in a 0.3% carboxymethyl cellulose-containing saline solution. T/C was calculated in the same manner as in above b(i) and b(ii).

TABLE 7

| Compound No. | Dose (mg/kg) | T/C Tumor Weight (%) | T/C Survival Days (%) |
|---|---|---|---|
| 13 | 250 | 0 | 127.8 |
|  | 100 | 2.6 | 194.4 |
|  | 50 | 156.6 | 120.0 | e. Effect on P-388 Lukemia (i) P-388 ascites cells ($1 \times 10^6$ cells/head) were inoculated intraperitoneally into BDF$_1$-strain mice (female, 6 weeks old, each group consisting of 4 mice), and after 24 hours, the intraperitoneal administration of a test drug was started and effected once a day for 7 days. The effect thereof was judged from the mean survival days. The test drug was used in the form of a solution or suspension in a saline solution or a 0.3% carboxymethyl cellulose-containing saline solution. T/C was calculated in the same manner as in above b(i).

TABLE 8

| Compound No. | Dose (mg/kg) | T/C (%) |
|---|---|---|
| 7 | 100 | 166.3 |

(ii) P-388 ascites cells ($1 \times 10^6$ cells/head) were inoculated subcutaneously at the right armpit into BDF$_1$-strain mice (male, 7 weeks old, each group consisting of 8 mice), and after 24 hours, the oral administration of a test drug was started, and effected once a day for 7 days. The effect thereof was judged from the mean weight of the tumor at the 11th day. The test drug was used in the form of a suspension or solution in a 0.3% carboxymethyl cellulose-containing saline solution or a dimethylsulfoxide-propylene glycol-phosphate buffer (1:2:1) mixture. T/C was calculated in the same manner as in above b(ii).

TABLE 9

| Compound No. | Dose (mg/kg) | T/C (%) |
|---|---|---|
| 4 | 50 | 79 |
| 13 | 200 | 49 |
|  | 60* | 25 |
| 41 | 200 | 67 |

Note:
*Solution in dimethylsulfoxide-propylene glycol-phosphate buffer (1:2:1) mixture f. Effect on Lewis Lung Carcinoma Lewis lung carcinoma cells ($1 \times 10^6$ cells/head) were inoculated subcutaneously at the right armpit region into BDF$_1$-strain mice (male, 6 weeks old, each group consisting of 5 mice) and after 24 hours, the oral administration of a test drug was started and effected once a day for 7 days. The effect thereof was judged from the average weight of tumor on the 21st day. The test drug was used in the form of a suspension in a 0.3% carboxymethyl cellulose-containing saline solution. T/C was calculated in the same manner as in above b(ii).

TABLE 10

| Compound No. | Dose (mg/kg) | T/C (%) |
|---|---|---|
| 13 | 100 | 73.2 |
|  | 200 | 67.1 |
| 41 | 100 | 65.9 |
|  | 200 | 43.4 | g. Effect on B-16 Melanoma

B-16 melanoma cells ($1 \times 10^6$ cells/head) were inoculated subcutaneously at the right armpit region into BDF$_1$-strain mice (male, 7 weeks old, each group consisting of 8 mice), and after 24 hours, the oral administration or subcutaneous administration at the dorsal region of a test drug was started and effected once a day for 3, 7 or 9 days. The effect thereof was judged from the mean weight of the tumor at the 18th, 19th or 21st day, respectively. The test drug was used in the form of a suspension or solution in a 0.3% carboxymethyl cellulose-containing saline solution or dimethylsulfoxide-propylene glycol (1:1) mixture. T/C was calculated in the same manner as in above b(ii).

TABLE 11

| Compound No. | Administration Route | Dose (mg/kg) | Number of Administrations | T/C (%) | Judgement Day |
|---|---|---|---|---|---|
| 4 | Orally | 100 | 7 | 58 | 18th |
|  |  | 50 | 9 | 60 | 21st |
|  |  | 50* | 7 | 71 | 19th |
|  | Subcutaneously | 25 | 7 | 38 | 19th |
| 13 | Orally | 100 | 7 | 62 | 18th |
|  |  | 200 | 9 | 23 | 21st |
|  |  | 100* | 7 | 40 | 19th |
|  | Subcutaneously | 50* | 7 | 88 | 19th |
| 41 | Orally | 100 | 7 | 88 | 18th |
|  |  | 100* | 7 | 43 | 19th |
|  | Subcutaneously | 50 | 3 | 37 | 19th |

Note:
*Dissolved in a dimethylsulfoxide-propylene glycol (1:1) mixture.

B. Acute Toxicity

Each of the test drugs was administered intraperitoneally once to ICR-strain mice (male, 6 weeks old, each group consisting of 5 mice), and the mice were observed for 7 days.

The test drugs were used in the form of a solution or suspension in a saline solution or a 0.3% carboxymethyl cellulose-containing saline solution.

TABLE 12

| Compound No. | LD$_{50}$ (mg/kg) | Compound No. | LD$_{50}$ (mg/kg) |
|---|---|---|---|
| 1 | >500 | 14 | >500 |
| 2 | >200 | 15 | >500 |
| 4 | >300 | 19 | >500 |
| 6 | >500 | 20 | >500 |
| 7 | >1000 | 41 | >200 |
| 12 | >500 | 42 | >200 |

TABLE 12-continued

| Compound No. | LD$_{50}$ (mg/kg) | Compound No. | LD$_{50}$ (mg/kg) |
|---|---|---|---|
| 13 | >1000 | 43 | >200 |
|  |  | 44 | >200 |

From the results shown above, it can be seen that the compounds represented by the formula (I) have such excellent properties that they are effective in any administration form against various tumors and are low in toxicity, and hence, they are very useful.

A detailed explanation is made below of processes for producing the present compounds represented by the formula (I).

Production process (1)

A process for producing a 1-(4-aminobenzyl)-2,3-dioxopiperazine derivative represented by the formula:

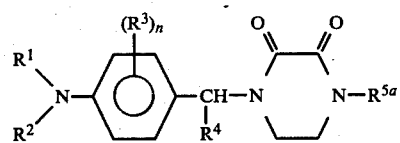
(IV)

wherein $R^1$, $R^2$, $R^3$, $R^4$ and n have the same meanings as defined above and $R^{5a}$ is a substituted or unsubstituted alkyl, alkenyl, alkadienyl, cycloalkyl, aralkyl, aryl or heterocyclic group, and an acid addition salt thereof, which comprises reacting a compound represented by the formula:

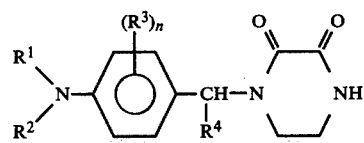
(II)

wherein $R^1$, $R^2$, $R^3$, $R^4$ and n have the same meanings as defined above, or a reactive derivative thereof, with a compound represented by the formula:

$$R^{5a}-Y \qquad (III)$$

wherein $R^{5a}$ has the same meaning as defined above, and Y represents a reactive group.

Production process (2)

A process for producing a 1-(4-aminobenzyl)-2,3-dioxopiperazine derivative represented by the formula:

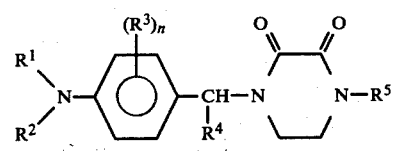
(I)

wherein $R^1$, $R^2$, $R^3$, $R^4$, $R^5$ and n have the same meanings as defined above, and an acid addition salt thereof, which comprises reacting a compound represented by the formula:

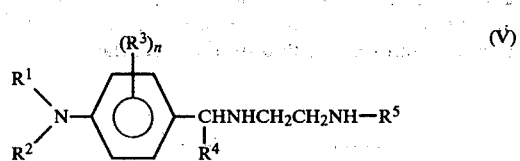
(V)

wherein $R^1$, $R^2$, $R^3$, $R^4$, $R^5$ and n have the same meanings as defined above, with an oxalic acid derivative represented by the formula:

(VI)

wherein X represents a reactive group.

Production process (3)

A process for producing a 1-(4-aminobenzyl)-2,3-dioxopiperazine derivative represented by the formula:

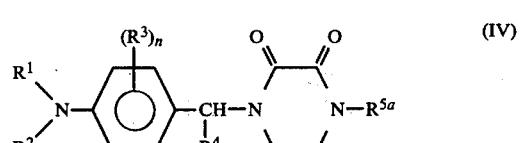
(IV)

wherein $R^1$, $R^2$, $R^3$, $R^4$, $R^{5a}$ and n have the same meanings as defined above, and an acid addition salt thereof, which comprises reacting a compound represented by the formula:

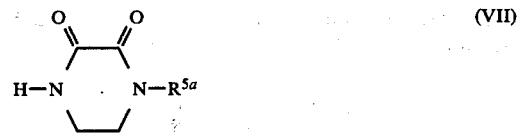
(VII)

wherein $R^{5a}$ has the same meaning as defined above, or a reactive derivative thereof, with a compound represented by the formula:

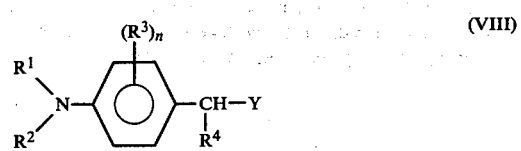
(VIII)

wherein $R^1$, $R^2$, $R^3$, $R^4$, n and Y have the same meanings as defined above.

Production process (4)

A process for producing a 1-(4-aminobenzyl)-2,3-dioxopiperazine derivative represented by the formula:

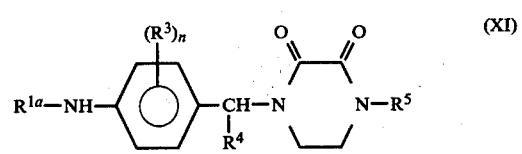
(XI)

wherein $R^3$, $R^4$, $R^5$ and n have the same meanings as defined above, and $R^{1a}$ is a substituted or unsubstituted alkyl, cycloalkyl, aralkyl, acyl or heterocyclic group or an acid addition salt thereof, which comprises reacting a compound represented by the formula:

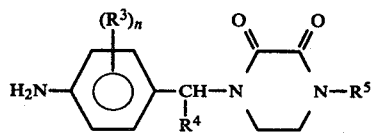 (IX)

wherein $R^3$, $R^4$, $R^5$ and n have the same meanings as defined above or a reactive derivative thereof, with a compound represented by the formula:

$R^{1a}-Y^1$ (X)

wherein $R^{1a}$ has the same meaning as defined above, and $Y^1$ represents a reactive group.

Production process (5)

A process for producing a 1-(4-aminobenzyl)-2,3-dioxopiperazine derivative represented by the formula:

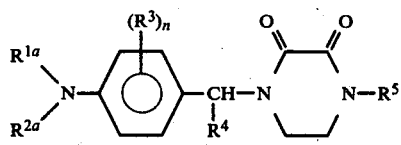 (XIII)

wherein $R^{1a}$, $R^3$, $R^4$, $R^5$ and n have the same meanings as defined above and $R^{2a}$ represents a substituted or unsubstituted alkyl, cycloalkyl, aralkyl, acyl or heterocyclic group, and an acid addition salt thereof, which comprises reacting a compound represented by the formula:

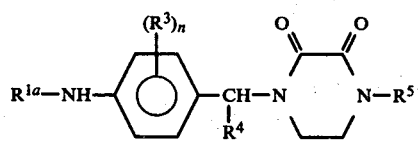 (XI)

wherein $R^{1a}$, $R^3$, $R^4$, $R^5$ and n have the same meanings as defined above, or a reactive derivative thereof, with a compound represented by the formula:

$R^{2a}-Y^1$ (XII)

wherein $R^{2a}$ and $Y^1$ have the same meanings as defined above.

Production process (6)

A process for producing a 1-(4-aminobenzyl)-2,3-dioxopiperazine derivative represented by the formula:

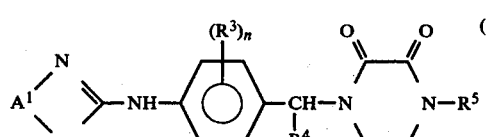 (XV)

wherein $R^3$, $R^4$, $R^5$ and n have the same meanings as defined above; $A^1$ represents an alkenylene group or a substituted or unsubstituted alkylene or phenylene group; and W represents a sulfur atom or an imino group, or an acid addition salt thereof, which comprises subjecting to ring closure in the presence of an acid or a base, a compound represented by the formula:

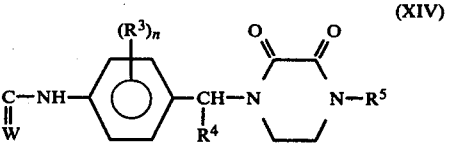 (XIV)

wherein $R^3$, $R^4$, $R^5$, n and W have the same meanings as defined above; A represents a substituted or unsubstituted alkylene or phenylene group; and Z represents an amino or dialkoxymethyl group, or a reactive derivative thereof.

Production process (7)

A method for producing a 1-(4-aminobenzyl)-2,3-dioxopiperazine derivative represented by the formula:

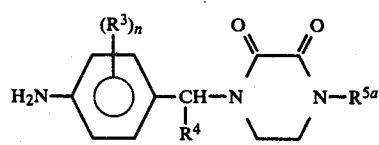 (XVIII)

wherein $R^3$, $R^4$, $R^{5a}$ and n have the same meanings as defined above, or an acid addition salt thereof, which comprises reacting a compound represented by the formula:

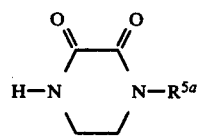 (VII)

wherein $R^{5a}$ has the same meaning as defined above, or a reactive derivative, with a compound represented by the formula:

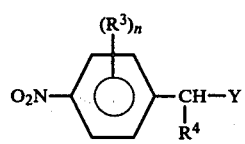 (XVI)

wherein $R^3$, $R^4$, Y and n have the same meanings as defined above, to obtain a compound represented by the formula:

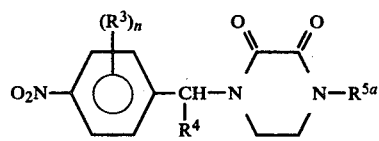 (XVII)

wherein $R^3$, $R^4$, $R^{5a}$ and n have the same meanings as defined above, and then reducing the compound thus obtained.

The compounds of this invention can be produced by, for example, the above-mentioned 7 processes. In each of the processes, $R^1$, $R^2$, $R^3$, $R^4$, $R^5$ and n have the same meanings as defined above, and examples of $R^{1a}$ or $R^{2a}$ in the formulas (X), (XI), (XII) and (XIII) include the same alkyl, cycloalkyl, aralkyl, acyl and heterocyclic groups mentioned for $R^1$ or $R^2$, and $R^{1a}$ and $R^{2a}$ may be substituted by the same substituents as mentioned for $R^1$ and $R^2$. Examples of $R^{5a}$ in the formulas (III), (IV), (VII), (XVII) and (XVIII) include the same alkyl, alkenyl, alkadienyl, cycloalkyl, aralkyl, aryl and heterocyclic groups as mentioned for $R^5$, and may be substituted by the same substituents as mentioned for $R^5$.

As the reactive group for Y in the formulas (III), (VIII) and (XVI), there may be mentioned halogen atoms such as chlorine, bromine, iodine, and the like; arylsulfonyloxy groups such as p-toluenesulfonyloxy, phenylsulfonyloxy, and the like; and alkylsulfonyloxy groups such as methanesulfonyloxy, ethanesulfonyloxy, and the like. As the reactive group for X in the formula (VI), in which X's may be the same or different, there may be mentioned, for example, alkoxy groups such as methoxy, ethoxy, and the like; and halogen atoms such as chlorine and the like.

As the reactive group for $Y^1$ in the formulas (X) and (XII), there may be mentioned halogen atoms such as chlorine, bromine, iodine, and the like; arylsulfonyloxy groups such as p-toluenesulfonyloxy, phenylsulfonyloxy, and the like; alkylsulfonyloxy groups such as methanesulfonyloxy, ethanesulfonyloxy, and the like; alkoxy groups such as methoxy, ethoxy, and the like; and alkylthio groups such as methylthio, ethylthio, and the like. In the formulas (XIV) and (XV), A may be an alkylene, preferably $C_{1-3}$ alkylene, group such as methylene, ethylene, propylene, or the like; a phenylene group, or the like, and these groups may be substituted by at least one substituent, for example, a halogen atom such as fluorine, chlorine, bromine, iodine or the like; a hydroxyl group; a carboxyl group; a $C_{1-4}$ alkoxycarbonyl group such as methoxycarbonyl, ethoxycarbonyl or the like; an ar-$C_{1-4}$ alkyloxycarbonyl group such as benzyloxycarbonyl or the like; an aryloxycarbonyl group such as phenoxycarbonyl or the like; a $C_{1-4}$ alkyl group such as methyl, ethyl, propyl, isopropyl, butyl, or the like; a $C_{2-4}$ alkenyl group such as vinyl, allyl, or the like; an ar-$C_{1-4}$ alkyl group such as benzyl, phenethyl, or the like; a $C_{5-6}$ cycloalkyl group such as cyclopentyl, cyclohexyl, or the like; a cyano group; a mercapto group; a $C_{1-4}$ alkylthio group such as methylthio, ethylthio, or the like; a nitro group; a $C_{1-4}$ alkanoylamino group such as acetamido or the like; a $C_{1-4}$ alkoxy group such as methoxy, ethoxy, or the like; an ar-$C_{1-4}$ alkyloxy group such as benzyloxy or the like; a $C_{1-8}$ acyl group such as formyl, acetyl, propionyl, butyryl, benzoyl, or the like; an amino group; a $C_{1-4}$ alkylamino group such as methylamino, ethylamino, or the like; a dialkylamino such as dimethylamino, diethylamino, or the like; an arylamino group such as anilino, or the like; a heterocyclic group such as pyridyl, pyrimidinyl, imidazolyl, thiazolyl, pirazinyl, oxazolyl, furyl, thienyl, pyrrolyl, pyridazinyl, or the like. As the dialkoxymethyl group for Z, di-$C_{1-4}$ alkoxymethyl groups such as dimethoxymethyl, diethoxymethyl, and the like may be used, and as $A^1$ $C_{2-4}$ alkenylene may be used such as vinylene, propenylene, or the like.

In each of the above-mentioned production methods, the reactive derivatives of the compounds represented by the formulas (II), (VII), (IX), (XI) and (XIV) include compounds formed by bonding an alkali metal atom such as lithium, sodium, potassium, or the like; a silyl compound such as $(CH_3)_3Si-$, $(CH_3)_2Si<$, $(CH_3)_2[(CH_3)_2CH]Si-$, $(CH_3O)_3Si-$, $CH_3(CH_3O)_2Si-$, $(CH_3)_2(CH_3O)Si-$, or the like; or a phosphorus compound such as $(CH_3O)_2P-$, $(C_2H_5O)_2P-$,

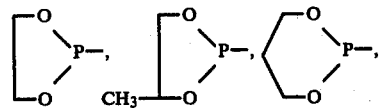

or the like, to the >NH or —$NH_2$ group which is a reaction site in the above-mentioned formulas. These reactive derivatives can easily be synthesized according to a conventional method, and may be subjected without isolation to the subsequent reaction.

The compounds represented by the formulas (II), (V), (IX), (XIV) and (XVII) which are the starting materials in the production method of this invention can be produced by various processes, among which representative are, for example, the above-mentioned processes of this invention and the processes which are through the following reaction routes:

Reaction Routes

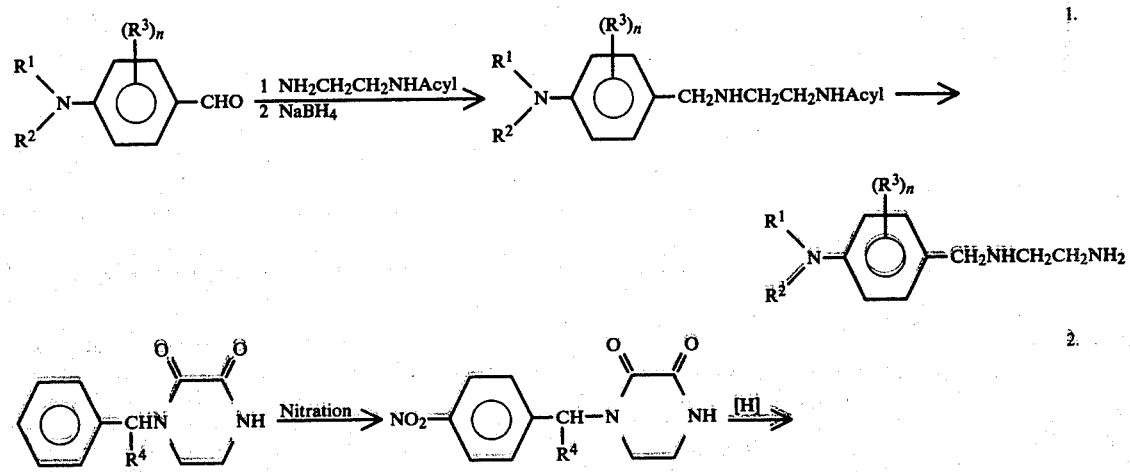

-continued
Reaction Routes

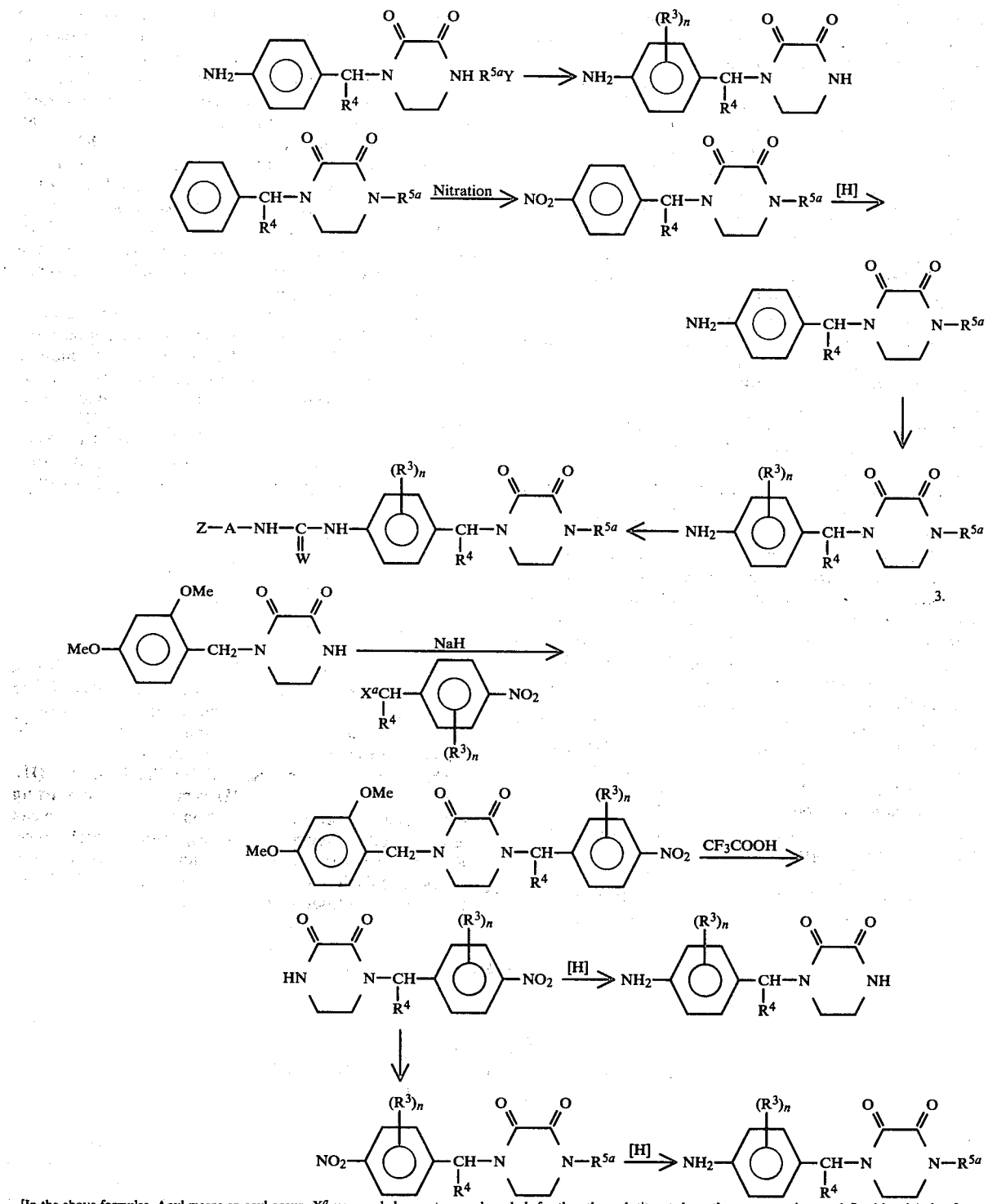

[In the above formulas, Acyl means an acyl group; $X^a$ means a halogen atom; and symbols for the other substituents have the same meanings as defined hereinbefore.]

Embodiments of each production process are described below.

The production processes (1) and (3) are carried out similarly in the presence or absence of a solvent inert to the reaction. The solvent used in the reaction includes, for example, ethers such as tetrahydrofuran, diethyl ether, dimethoxyethyl ether, dimethoxyethane, dioxane, and the like; halogenated hydrocarbons such as methylene chloride, chloroform, 1,2-dichloroethane, and the like; alcohols such as methanol, ethanol, isopropanol, tert-butyl aocohol, tert-amyl alcohol, ethylene glycol, ethylene glycol monomethyl ether, and the like; amides such as dimethylformamide, dimethylacetamide, and the like; nitriles such as acetonitrile, propionitrile, and the like; aromatic hydrocarbons such as benzene, toluene, xylene, and the like; nitroalkanes such as nitromethane, nitroethane, and the like; tertiary amines such as pyridine, quinoline, and the like; sulfoxides such as dimethylsulfoxide and the like; and phosphoric amides such as hexamethylphosphoric amide and the like. The above-mentioned solvents may be used also in admixture of two or more.

The reaction temperature and the reaction time are not critical, though the reaction is preferably effected at 0° to 150° C., and in this case, the reaction is usually completed in 5 minutes to 12 hours. The reaction is usually effected at atmospheric pressure, though desirable results are sometimes obtained when the reaction is effected under pressure in a sealed tube or an autoclave. The compounds represented by the formulas (III) and (VII) are used in quantities at least equimolar to, preferably of 1.0 to 1.2 moles per mole of, the compounds represented by the formulas (II) and (VIII), respectively.

The production process (2) is carried out in the presence or absence of a solvent inert to the reaction. The solvent used in the reaction includes, for example, alcohols such as methanol, ethanol, isopropanol, and the like; ethers such as tetrahydrofuran, diethyl ether, dioxane, dimethoxyethane, and the like; aromatic hydrocarbons such as benzene, toluene, xylene, and the like; nitroalkanes such as nitromethane, nitroethane, and the like; nitriles such as acetonitrile, propionitrile, and the like; amides such as dimethylformamide, dimethylacetamide, and the like; and halogenated hydrocarbons such as methylene chloride, chloroform, and the like. These solvents may be used also in admixture of two or more. The reaction temperature and the reaction time are not critical, though the reaction is preferably effected at 0° to 150° C., and in this case, the reaction is usually completed in 30 minutes to 24 hours. The oxalic acid derivative represented by the formula (VI) is used in a quantity of usually 1 to 1.5 moles, preferably 1 to 1.2 moles, per mole of the compound represented by the formula (V).

The production processes (4) and (5) are carried out similarly in the presence or absence of a solvent inert to the reaction. The solvent used in the reaction is the same as used in the above-mentioned production methods (1) and (3). The reaction temperature and the reaction time are not critical though the reaction is preferably effected at room temperature to 150° C., and in this case, the reaction is completed in 5 minutes to 12 hours. The reaction is usually effected at atmospheric pressure, though desirable results are sometimes obtained when the reaction is effected under pressure in a sealed tube or an autoclave. The compound represented by the formula (X) is used in a quantity at least equimolar to, preferably of 1.0 to 1.2 moles per mole of, the compound represented by the formula (IX). The compound represented by the formula (XII) is used in a quantity at least equimolar to, preferably of 1.0 to 2.0 moles per mole of, the compound represented by the formula (XI). In the production processes (1) to (5), a deacidifying agent or a catalyst may be used. In this case, as usable deacidifying agents, there may be mentioned, for example, tertiary amines such as triethylamine, pyridine, quinoline, N-methylmorpholine, diethylaniline, 4-dimethylaminopyridine, and the like; and inorganic bases such as potassium carbonate, sodium carbonate, sodium hydrogen carbonate, and the like. As the catalyst, metals such as activated copper and the like may be used.

The production process (6) is carried out in the presence or absence of a solvent inert to the reaction. The solvent used in the reaction includes acetone, dialkyl ketones such as methyl ethyl ketone, diisobutyl ketone, and the like in addition to the solvents mentioned above regarding production processes (1) and (3). The reaction temperature and the reaction time are not critical, though the reaction is preferably effected at 0° to 150° C., and in this case, the reaction is completed in 5 minutes to 12 hours. The acid used includes, for example, inorganic acids such as hydrochloric acid, hydrobromic acid, hydroiodic acid, sulfuric acid, nitric acid, and the like; and organic acids such as formic acid, acetic acid, propionic acid, and the like. The base used includes, for example, tertiary amines such as pyridine, triethylamine, trimethylamine, N-methylpiperidine, N-methylmorpholine, and the like; and inorganic bases such as sodium hydrogencarbonate, potassium carbonate, potassium hydrogencarbonate, barium hydroxide, and the like. These acids or bases are usually used in a quantity of 1.0 to 2.0 moles per mole of the compound represented by the formula (XIV).

The production process (7) is carried out similarly in the presence or absence of a solvent inert to the reaction. The solvent used in the reaction includes, for example, ethers such as tetrahydrofuran, diethyl ether, dimethoxyethyl ether, dimethoxyethane, dioxane, and the like; halogenated hydrocarbons such as methylene chloride, chloroform, 1,2-dichloroethane, and the like; alcohols such as methanol, ethanol, isopropanol, tert-butyl alcohol, tert-amyl alcohol, ethylene glycol, ethylene glycol monomethyl ether, and the like; amides such as dimethylformamide, dimethylacetamide, and the like; nitriles such as acetonitrile, propionitrile, and the like; aromatic hydrocarbons such as benzene, toluene, xylene, and the like; nitroalkanes such as nitromethane, nitroethane, and the like; tertiary amines such as pyridine, quinoline, and the like; sulfoxides such as dimethylsulfoxide and the like; and phosphoric amides such as hexamethylphosphoric amide and the like. The above-mentioned solvents may be used also in admixture of two or more.

The reaction temperature and the reaction time are not critical, though the reaction is preferably effected at 0° to 150° C., and in this case, the reaction is usually completed in 5 minutes to 12 hours. The reaction is usually effected at atmospheric pressure, though desirable results are sometimes obtained when the reaction is effected under pressure in a sealed tube or an autoclave. The compound represented by the formula (VII) is used in a quantity at least equimolar to, preferably of 1.0 to 1.2 moles per mole of, the compound represented by the formula (XVI). When reacting the compound of the formula (VII) with the compound of the formula (XVI), a deacidifying agent may be used. The deacidifying agent includes, for example, tertiary amines, such as, triethylamine, pyridine, quinoline, N-methylmorpholine, diethylaniline, 4-dimethylaminopyridine and the like and inorganic bases such as potassium carbonate, sodium carbonate, sodium hydrogencarbonate and the like.

Subsequently, the compound of the formula (XVII) is subjected to conventional reduction in the presence of a solvent inert to the reaction. The solvent used in the reaction includes, for example, water; alcohols such as methanol, ethanol, isopropanol, tert-butyl alcohol, tert-amyl alcohol, ethylene glycol, ethylene glycol monomethyl ether, and the like; and fatty acids such as acetic acid, propionic acid, and the like. The above-mentioned solvents may be used also in admixture of two or more. The conventional reduction includes, such as, hydrogenation with palladium-carbon, reduction with zinc powder, or the like.

The reaction temperature and the reaction time are not critical, though the reaction is preferably effected at 0° to 150° C., and in this case, the reaction is usually completed in several hours.

After the reaction is effected in the manner described above, the compound represented by the formula (I) can be isolated from the reaction mixture according to a conventional method, and purified by procedures such as column chromatography, recrystallization, and the like. An acid addition salt of the compound represented by the formula (I) can be obtained by effecting the reaction according to a conventional method using an inorganic acid such as hydrochloric acid, hydrobromic acid, hydroiodic acid, or the like, or an organic acid such as p-toluenesulfonic acid, acetic acid, or the like, and then isolating and purifying the reaction product. In the above-mentioned production methods, when the compounds represented by the formulas (II), (III), (V), (VII), (VIII), (IX), (X), (XI), (XII), (XIV), (XVI), and (XVII) have an active group such as amino, hydroxyl, carboxyl, or the like in the unreactive site, compounds having a protecting group can be obtained by protecting the active group with a well-known protecting group, and then carrying out the method of this invention, and a compound having a free active group can be obtained by treating the compound having a protecting group by a well-known method to release the protecting group.

The compounds represented by the formula (I) and their acid addition salts of this invention are applicable to various cancers, for example, solid tumor, leukemia, and the like. In using the compound of this invention, a carrier which is usually used in a carcinostatic agent may be added thereto, and the mixture is formulated into various drug forms, such as tablets, syrup, capsules, powder, an injection and the like.

When the compound of this invention is actually administered to a man, the administration route, the dosage, and the number of administrations are properly selected depending upon the conditions of a patient, though, in general, it is sufficient that the compound is administered once to thrice a day in a dosage of 1 to 4000 mg/kg per day per adult by injection (intravenous injection, intramuscular injection, intraarterial injection, intravenous drip injection, etc.) or orally. The compound of this invention may be administered either every day or intermittently, and may be used together with other carcinostatic agents.

This invention is further explained below referring to Examples, which are merely illustrative and not limitative.

EXAMPLE 1

(1) In 1.3 liters of methanol was suspended 326 g of p-acetamidobenzaldehyde, and 204 g of N-acetylethylenediamine was added dropwise thereto over a period of one hour.

Subsequently, the resulting mixture was refluxed for one hour, after which 75.7 g of sodium borohydride was added to the mixture with ice-cooling over a period of one hour. After the completion of the addition, the mixture thus obtained was allowed to stand overnight at room temperature, after which the solvent was removed by distillation under reduced pressure. One liter of concentrated hydrochloric acid was added dropwise to the resulting oily residue with ice-cooling over a period of one hour. After the completion of the addition, the resulting mixture is refluxed for 2 hours. To the mixture was gradually added 700 g of sodium hydroxide with ice-cooling to make the mixture strongly basic, after which the mixture was extracted with one liter of dioxane. The dioxane layer obtained was dried over sodium hydroxide, and the dioxane was thereafter removed by distillation under reduced pressure. The oily residue thus obtained was distilled under reduced pressure to obtain 218 g (66.1% yield) of N-(4-aminobenzyl)ethylenediamine (b.p. 150° to 156° C./3 mmHg).

(2) To 1.5 liters of ethanol was added 179 ml of diethyl oxalate, followed by adding dropwise to the resulting solution 700 ml of an ethanol solution containing 218 g of the N-(4-aminobenzyl)ethylenediamine obtained in above (1) under reflux over a period of 2 hours. After the completion of the addition, the resulting mixture was refluxed for a further one hour and then allowed to stand overnight at room temperature. Subsequently, the crystals thus precipitated were collected by filtration, and then recrystallized from dimethylformamide (hereinafter referred to as DMF) to obtain 173 g (59.9% yield) of 1-(4-aminobenzyl)-2,3-dioxopiperazine having a melting point of 246° to 249° C.

IR(KBr)cm$^{-1}$: $\nu_{NH}$: 3475, 3375, 3220, $\nu_{C=O}$: 1710, 1680, 1655.

EXAMPLE 2

In 30 ml of methanol was dissolved 0.13 g of metallic sodium, followed by adding thereto 1.0 g of 1-(2,4-dichloro-5-pyrimidinylmethyl)-4-(4-diethylaminobenzyl)-2,3-dioxopiperazine. The resulting mixture was subjected to reaction under reflux for 1.5 hours. After the completion of the reaction, 1 ml of glacial acetic acid was added to the mixture, after which the solvent was removed by distillation under reduced pressure, and the resulting residue was extracted with 20 ml of chloroform. The chloroform layer was washed with water and then a saturated aqueous sodium chloride solution, and then dried over anhydrous magnesium sulfate, after which the solvent was removed by distillation under reduced pressure. The crystals thus obtained were recrystallized from ethyl acetate-diisopropyl ether to obtain 0.9 g (91.8% yield) of pale yellow crystals of 1-(4-diethylaminobenzyl)-4-(2,4-dimethoxy-5-pirimidinylmethyl)-2,3-dioxopiperazine having a melting point of 111.5° to 113° C.

IR(KBr)cm$^{-1}$: $\nu_{C=O}$: 1665.

EXAMPLE 3

(1) With 1.1 g of sodium hydride (50% purity) was mixed 50 ml of DMF, and 4.6 g of 1-n-hexyl-2,3-dioxopiperazine was added thereto with stirring at room temperature over a period of 10 minutes. Subsequently, the resulting mixture was subjected to reaction at 50° to 60° C. for 30 minutes, and 5.5 g of p-nitrobenzyl bromide was added to the reaction mixture over a period of 10 minutes, after which the mixture thus obtained was further subjected to reaction at 50° to 60° C. for 2 hours. The solvent was removed by distillation under reduced pressure. The residue was extracted with 70 ml of ethyl acetate, and the ethyl acetate layer was washed with water and then a saturated aqueous sodium chloride solution, and then dried over anhydrous magnesium sulfate, after which the solvent was removed by distillation under reduced pressure. The crystals thus obtained were recrystallized from isopropyl alcohol to obtain 4.0 g (51.9% yield) of 1-n-hexyl-4-(4-nitrobenzyl)-2,3-dioxopiperazine having a melting point of 115° to 117° C.

IR(KBr)cm$^{-1}$: $\nu_{C=O}$: 1670.

(2) In 150 ml of 50% by weight hydrous ethanol was suspended 4.5 g of the 1-n-hexyl-4-(4-nitrobenzyl)-2,3-dioxopiperazine obtained in above (1), followed by adding thereto 22.5 g of zinc powder and then 5 ml of an aqueous solution containing 4.5 g of calcium chloride. The resulting solution was subjected to reaction under reflux for 2 hours. After the completion of the reaction, the reaction mixture was filtered through celite, and the solvent in the filtrate was removed by distillation under reduced pressure, after which the resulting residue was extracted with 50 ml of ethyl acetate. The ethyl acetate layer was washed with water and then a saturated aqueous sodium chloride solution, and then dried over anhydrous magnesium sulfate, and the solvent was removed by distillation under reduced pressure. The crystals thus obtained were recrystallized from isopropyl alcohol to obtain 2.7 g (65.9% yield) of 1-(4-aminobenzyl)-4-n-hexyl-2,3-dioxopiperazine having a melting point of 99° to 101.5° C.

IR(KBr)cm$^{-1}$: $\nu_{NH}$; 3345, 3420, $\nu_{C=O}$; 1665.

EXAMPLE 4

(1) In 100 ml of chloroform were dissolved 2.3 g of ethylenediamine and 11.9 ml of triethylamine, followed by adding thereto 50 ml of a chloroform solution containing 15 g of 4-diethylaminobenzoyl chloride with ice-cooling over a period of 30 minutes. Subsequently, the resulting mixture was subjected to reaction at room temperature for 2 hours, after which 100 ml of water was added to the mixture. The chloroform layer was washed with a saturated aqueous sodium chloride solution, and then dried over anhydrous magnesium sulfate, and the solvent was removed by distillation under reduced pressure. The crystals thus obtained were recrystallized from isopropyl alcohol-diisopropyl ether to obtain 9.8 g (62.4% yield) of N,N'-bis(4-diethylaminobenzoyl)ethylenediamine having a melting point of 166° to 167° C.

IR(KBr)cm$^{-1}$: $\nu_{NH}$; 3290, $\nu_{C=O}$; 1605.

(2) In 200 ml of anhydrous tetrahydrofuran were suspended 15.7 g of N,N'-bis(4-diethylaminobenzoyl)ethylenediamine obtained in above (1) and 5.4 g of sodium borohydride, followed by adding dropwise thereto 24 ml of a boron trifluoride-diethyl ether complex (47% purity) with stirring at a temperature of not more than 10° C. over a period of 30 minutes. Subsequently, the resulting mixture was refluxed for 4 hours, after which 30 ml of methanol was added dropwise to the mixture with ice-cooling over a period of 30 minutes. The reaction mixture was filtered through celite, and the solvent in the filtrate was removed by distillation under reduced pressure, after which the thus obtained oily residue was dissolved in 200 ml of ethanol, and hydrogen chloride gas was introduced into the resulting solution with ice-cooling until the solution reached saturation. Subsequently, the solution was refluxed for one hour and then allowed to stand. The crystals thus precipitated were collected by filtration, and then dissolved in 50 ml of water, and the pH of the solution thus obtained was adjusted to 14 with calcium hydroxide. The solution was extracted with 50 ml of methylene chloride, and the extract was washed with a saturated aqueous sodium chloride solution, and then dried over anhydrous calcium carbonate, after which the solvent was removed by distillation under reduced pressure to obtain 5.0 g (33.8% yield) of oily N,N'-bis(4-diethylaminobenzyl)ethylenediamine.

(3) To 100 ml of ethanol were added dropwise 20 ml of an ethanol solution containing 5.0 g of the N,N'-bis-(4-diethylaminobenzyl)ethylenediamine obtained in above (2) and 20 ml of an ethanol solution containing 1.9 g of diethyl oxalate with stirring at room temperature over a period of 20 minutes. Subsequently, the resulting mixture was refluxed for 2 hours, after which the solvent was removed by distillation under reduced pressure. The crystals thus obtained were recrystallized from ethanol to obtain 5.0 g (87.7% yield) of white crystals of 1,4-bis(4-diethylaminobenzyl)-2,3-dioxopiperazine having a melting point of 166° to 167.5° C.

IR(KBr)cm$^{-1}$: $\nu_{C=O}$; 1655.

EXAMPLE 5

To 100 ml of benzene were added 3.5 g of 1-aminoethyl-4-(4-diethylaminobenzyl)-2,3-dioxopiperazine and 1.9 g of 4-diethylaminobenzaldehyde, and the resulting mixture was subjected to reaction with azeotropic dehydration for 5 hours. After the completion of the reaction, the solvent was removed by distillation under reduced pressure, and the resulting residue was dissolved in 100 ml of methanol. To the resulting solution was added 0.6 g of sodium borohydride with ice-cooling, and the mixture thus obtained was allowed to stand at room temperature for one hour. The solvent was removed by distillation under reduced pressure, and the residue thus obtained was extracted with 100 ml of chloroform. The extract was washed successively with water and a saturated aqueous sodium chloride solution, and then dried over anhydrous potassium carbonate, after which the solvent was removed by distillation under reduced pressure. The resulting residue was purified by column chromatography (Merk Art. 1076, eluted with chloroform), and then dissolved in ethanol, and hydrogen chloride gas was introduced in excess into the resulting solution, after which the solvent was removed by distillation under reduced pressure. The crystals thus obtained were recrystallized from methanol-isopropanol to obtain 1.2 g (18.5% yield) of white crystals of 1-(4-diethylaminobenzyl)-4-(4-diethylaminobenzylaminoethyl)-2,3-dioxopiperazine trihydrochloride having a melting point of 220° to 221° C.

IR(KBr)cm$^{-1}$: $\nu_{C=O}$; 1660.

EXAMPLE 6

(1) In 50 ml of DMF were dissolved 21.6 g of 2-bromopyrimidine and 30 g of 1-(4-aminobenzyl)-2,3-dioxopiperazine, and the resulting solution was subjected to reaction at 130° to 140° C. for 30 minutes. After the completion of the reaction, a saturated aqueous sodium hydrogencarbonate solution was added to the reaction mixture and the yellow crystals thus precipitated were collected by filtration. The crystals were recrystallized from hot water to obtain 28 g (68.8% yield) of pale yellow crystals of 1-[4-(2-pyrimidinylamino)benzyl]-2,3-dioxopiperazine having a melting point of 253° C.

IR(KBr)cm$^{-1}$: $\nu_{NH}$; 3200, 3120, $\nu_{C=O}$; 1660.

Elementary analysis (for $C_{15}H_{15}N_5O_2$); Calcd. (%) C: 60.59, H: 5.09, N: 23.56; Found (%) C: 60.25, H: 5.07, N: 23.10.

NMR(d$_6$-DMSO) ppm values:
3.45 (4H, bs, piperazine ring >CH$_2$×2)
4.61 (2H, s, >CH$_2$×1)
6.88 (1H, t, J=4.5 Hz, pyrimidine ring H×1)
7.30 (2H, d, J=8.5 Hz, benzene ring H×2)
7.84 (2H, d, J=8.5 Hz, benzene ring H×2)
8.52 (2H, d, J=4.5 Hz, pyrimidine ring H×2)
8.39–8.69 (1H, bs, >NH×1)
9.57 (1H, s, >NH×1)

(2) To a suspension of 480 mg of sodium hydride (50% purity) in 30 ml of DMF was added 3 g of 1-[4-(2-pyrimidinylamino)benzyl]-2,3-dioxopiperazine with stirring, and the resulting mixture was subjected to reaction at room temperature for 30 minutes. Subsequently, a suspension of 1.4 g of benzyl chloride in 5 ml of DMF was added dropwise to the reaction mixture, and the mixture thus obtained was further subjected to reaction at 80° to 90° C. for one hour. After the completion of the reaction, the solvent was removed by distillation under reduced pressure, and the residue obtained was extracted with 100 ml of chloroform, and the extract was then washed with water. The chloroform layer was dried over anhydrous magnesium sulfate, after which the solvent was removed by distillation under reduced pressure, and the crystals thus obtained were recrystallized from ethanol to obtain 3.5 g (90% yield) of yellow crystals of 1-benzyl-4-[4-(2-pyrimidinylamino)benzyl]-2,3-dioxopiperazine having a melting point of 175° to 176° C.

IR(KBr)cm$^{-1}$: $\nu_{NH}$ 3320, $\nu_{C=O}$ 1670.

Elementary analysis (for C$_{22}$H$_{21}$N$_5$O$_2$); Calcd. (%) C: 68.20, H: 5.46, N: 18.08; Found (%) C: 68.24, H: 5.38, N: 17.89.

NMR(d$_6$-DMSO) ppm values:
3.42 (4H, bs, piperazine ring >CH$_2$×2)
4.51 (2H, s, >CH$_2$×1)
4.54 (2H, s, >CH$_2$×1)
6.75 (1H, t, J=4.5 Hz, pyrimidine ring H×1)
7.15 (2H, d, J=8.5 Hz, benzene ring H×2)
7.25 (5H, s, benzene ring H×5)
7.70 (2H, d, J=8.5 Hz, benzene ring H×2)
8.40 (2H, d, J=4.5 Hz, pyrimidine ring H×2)
9.68 (1H, s, >NH)

EXAMPLE 7

In 10 ml of DMF were dissolved 1 g of 1-[4-(2-pyrimidinylamino)benzyl]-2,3-dioxopiperazine and 1.5 ml of iodobenzene, followed by adding thereto 0.5 g of potassium carbonate and 50 mg of activated copper, and the resulting mixture was subjected to reaction under a reflux for 4 hours. After the completion of the reaction, the solvent was removed by distillation under reduced pressure, and the residue thus obtained was extracted with 20 ml of chloroform, and the chloroform layer was washed successively with water and a saturated aqueous sodium chloride solution, and then dried over anhydrous magnesium sulfate, after which the solvent was removed by distillation under reduced pressure. The crystals thus obtained were recrystallized from chloroform-isopropanol to obtain 1 g (80% yield) of white needle crystals of 1-phenyl-4-[4-(2-pyrimidinylamino)benzyl]-2,3-dioxopiperazine having a melting point of 205° to 206° C.

IR(KBr)cm$^{-1}$: $\nu_{NH}$ 3300, $\nu_{C=O}$ 1675.

EXAMPLE 8

1-[2-(6-Acetamido)pyridylmethyl]-4-[4-(2-pyrimidinylamino)benzyl]-2,3-dioxopiperazine was hydrolyzed with 2 N hydrochloric acid to obtain white crystals of 1-[2-(6-amino)pyridylmethyl]-4-[4-(2-pyrimidinylamino)benzyl]-2,3-dioxopiperazine (83.3% yield).

IR(KBr)cm$^{-1}$: $\nu_{NH}$ 3120, 3190, 3275, $\nu_{C=O}$ 1670.

m.p. 225°–226° C. (recrystallized from chloroform-methanol)

EXAMPLE 9

In 10 ml of DMF were dissolved 2.86 g of 1-(4-aminobenzyl)-4-n-hexyl-2,3-dioxopiperazine and 1.5 g of 2-bromopyrimidine, and the resulting solution was subjected to reaction under reflux for 2 hours. After the completion of the reaction, the solvent was removed by distillation under reduced pressure, and the residue thus obtained was extracted with 50 ml of chloroform. The extract was washed successively with a saturated aqueous sodium hydrogencarbonate solution, water, and a saturated aqueous sodium chloride solution. The chloroform layer was dried over anhydrous magnesium sulfate, and the solvent was removed by distillation under reduced pressure. The crystals thus obtained were recrystallized from ethanol to obtain 2.7 g (75% yield) of white crystals of 1-n-hexyl-4-[4-(2-pyrimidinylamino)benzyl]-2,3-dioxopiperazine having a melting point of 159° to 160° C.

IR(KBr)cm$^{-1}$: $\nu_{NH}$ 3350, $\nu_{C=O}$ 1675.

Elementary analysis (for C$_{21}$H$_{27}$N$_5$O$_2$); Calcd. (%) C: 66.12, H: 7.13, N: 18.36; Found (%) C: 65.93, H: 7.07, N: 18.12.

NMR(d$_6$-DMSO-CDCl$_3$) ppm values:
0.83 (3H, m, —CH$_3$×1)
1.08–1.76 (8H, m, >CH$_2$×4)
3.23–3.63 (6H, m, piperazine ring >CH$_2$ and >CH$_2$×1)
4.53 (2H, s, >CH$_2$×1)
6.75 (1H, t, J=4.5 Hz, pyrimidine ring H×1)
7.16 (2H, d, J=8.5 Hz, benzene ring H×2)
7.72 (2H, d, J=8.5 Hz, benzene ring H×2)
8.39 (2H, d, J=4.5 Hz, pyrimidine ring H×2)
9.50 (1H, s, >NH×1)

EXAMPLE 10

In 5 ml of ethylene glycol were suspended 400 mg of 1-(4-ethylaminobenzyl)-4-n-hexyl-2,3-dioxopiperazine and 210 mg of 2-bromopyrimidine, and the resulting suspension was refluxed for 5 minutes. Subsequently, the suspension was allowed to stand at room temperature, and then extracted with 30 ml of chloroform, and the extract was washed successively with water and a saturated aqueous sodium chloride solution. The chloroform layer was dried over anhydrous magnesium sulfate, and the solvent was removed by distillation under reduced pressure. The residue thus obtained was purified by column chromatography (Wako gel C-200, eluted with chloroform), and then recrystallized from diethyl ether to obtain 100 mg (20.2% yield) of white crystals of 1-{4-[N-ethyl-N-(2-pyrmidinyl)]aminobenzyl}-4-n-hexyl-2,3-dioxopiperazine having a melting point of 79° to 81° C.

IR(KBr)cm$^{-1}$: $\nu_{C=O}$ 1673.

EXAMPLE 11

(1) In 16 ml of DMF were dissolved 5.85 g of 1-(4-aminobenzyl)-4-benzyl-2,3-dioxopiperazine and 3 g of 2-chloro-5-nitropyridine, and the resulting solution was subjected to reaction at 140° C. for one hour. After the completion of the reaction, 100 ml of water was added to the reaction mixture, and the crystals thus precipitated were collected by filtration. The crystals thus obtained were recrystallized from acetic acid to obtain 7 g (85.8% yield) of yellow crystals of 1-benzyl-4-[4-N-(5-nitro-2-pyridyl)aminobenzyl]-2,3-dioxopiperazine having a melting point of 202° to 204° C.

IR(KBr)cm$^{-1}$: $\nu_{NH}$; 3300, $\nu_{C=O}$; 1665, $\nu_{NO2}$; 1335.

(2) In 150 ml of acetic acid was suspended 7 g of the 1-benzyl-4-[4-N-(5-nitro-2-pyridyl)aminobenzyl]-2,3-dioxopiperazine obtained in above (1), followed by adding thereto 500 mg of 5% Pd-C, and the resulting mixture was subjected to reaction under a hydrogen stream with stirring at room temperature at atmospheric pressure for 2 hours. After the completion of the reaction, the reaction mixture was filtered through celite, and the solvent in the filtrate was removed by distillation under reduced pressure. The residue was extracted with 100 ml of 2 N hydrochloric acid, and the extract was washed with 100 ml of chloroform, adjusted to pH 8 with sodium hydrogen-carbonate, and then further extracted with 200 ml of chloroform.

The chloroform layer was washed successively with water and a saturated aqueous sodium chloride solution, and then dried over anhydrous magnesium sulfate, after which the solvent was removed by distillation under reduced pressure to obtain 5.6 g (86% yield) of redish violet crystals of 1-[4-N-(5-amino-2-pyridyl)aminobenzyl]-4-benzyl-2,3-dioxopiperazine.

m.p. 154°–155° C. (recrystallized from ethanol-diisopropyl ether)

IR(KBr)cm$^{-1}$: $\nu_{NH}$; 3340, $\nu_{C=O}$; 1670.

Elementary analysis (for $C_{23}H_{23}N_5O_2$); Calcd. (%) C: 68.81, H: 5.77, N: 17.44; Found (%) C: 68.64, H: 5.83, N: 17.09.

NMR(d$_6$-DMSO) ppm values:
3.39 (4H, bs, piperazine ring >CH$_2$×2)
4.15 (2H, bs, —NH$_2$×1)
4.45 (2H, s, >CH$_2$×1)
4.54 (2H, s, >CH$_2$×1)
6.63 (1H, d, J=9.5 Hz, pyridine ring H×1)
6.95 (1H, d, d, Jo=9.5 Hz, Jm=3 Hz, pyridine ring H×1)
7.04 (2H, J=9.5 Hz, benzene ring H×2)
7.24 (5H, bs, benzene ring H×5)
7.44 (2H, d, J=9.5 Hz, benzene ring H×2)
7.60 (1H, J=3 Hz, pyridine ring H×1)
8.45 (1H, s, >NH×1)

(3) In 100 ml of concentrated hydrochloric acid was dissolved 5.0 g of the 1-benzyl-4-[4-N-(5-nitro-2-pyridyl)aminobenzyl]-2,3-dioxopiperazine obtained in above (1). To the resulting solution was added 36 g of tin pieces and the resulting mixture was heated and stirred at 80° to 90° C. for 30 minutes. After the completion of the reaction, the reaction mixture was made weakly basic with ice-cooling with a 20% by weight aqueous sodium hydroxide solution, and then 50 ml of methanol and 400 ml of chloroform were added to the reaction mixture, after which the mixture thus obtained was shaken, and the insoluble matters were separated therefrom by filtration. After the insoluble matters were thoroughly washed with chloroform, the washings were combined with the previously obtained filtrate, and the organic layer was separated from the resulting mixture, washed with 50 ml of a saturated aqueous sodium chloride solution, and then dried over anhydrous sodium sulfate, after which the solvent was removed by distillation under reduced pressure. The residue was purified by column chromatography (Merk Art. 1076, developing solvent: chloroform) to obtain 2.1 g (44.7% yield) of amorphous crystals of 1-[4-N-(5-amino-2-pyridyl)aminobenzyl]-4-benzyl-2,3-dioxopiperazine (which agreed with the product obtained in the aforesaid (2) in melting point, IR and NMR) and 2.2 g (43.7%) of 1-[4-N-(5-amino-6-chloro-2-pyridyl)aminobenzyl]-4-benzyl-2,3-dioxopiperazine.

The 1-[4-N-(5-amino-6-chloro-2-pyridyl)aminobenzyl]-4-benzyl-2,3-dioxopiperazine was added to a saturated hydrogen chloride-ethanol solution, and the solvent was removed by distillation under reduced pressure, after which the residue was recrystallized from ethanol to obtain a hydrochloride thereof having a melting point of 237° to 238° C. (decomp.).

IR(KBr)cm$^{-1}$: $\nu_{C=O}$: 1660.

Elementary analysis (for $C_{23}H_{22}N_5O_2Cl.HCl$); Calcd. (%) C: 57.40, H: 5.04, N: 15.21; Found (%) C: 57.59, H: 5.18, N: 15.30.

NMR(CDCl$_3$) ppm values:
3.21 (4H, bs, piperazine ring >CH$_2$×2)
3.59 (2H, bs, —NH$_2$×1)
4.44 (2H, s, >CH$_2$×1)
4.51 (2H, s, >CH$_2$×1)
6.61 (1H, d, J=8.5 Hz, pyridine ring H×1)
7.1–7.23 (9H, m, pyridine H, benzene ring H×7, >NH×1)

EXAMPLE 12

(1) 1,4-Dibenzyl-2,3-dioxopiperazine was nitrated with concentrated sulfuric acid and concentrated nitric acid to obtain yellow crystals of 1,4-bis(4-nitrobenzyl)-2,3-dioxopiperazine (61% yield).

IR(KBr)cm$^{-1}$: $\nu_{C=O}$; 1670, $\nu_{NO2}$; 1330.

m.p. 257°–260° C. (recrystallized from DMF)

(2) The 1,4-bis(4-nitrobenzyl)-2,3-dioxopiperazine was subjected to the same reaction as in Example 3-(2) to obtain white crystals of 1,4-bis(4-aminobenzyl)-2,3-dioxopiperazine (46.9% yield).

IR(KBr)cm$^{-1}$: $\nu_{C=O}$; 1660.

m.p. 193°–194° C. (recrystallized from ethanol)

(3) The 1,4-bis(4-aminobenzyl)-2,3-dioxopiperazine was reacted with 2-bromopyrimidine in the same manner as in Example 6-(1) to obtain 1,4-bis[4-(2-pyrimidinylamino)benzyl]-2,3-dioxopiperazine (14.7% yield).

IR(KBr)cm$^{-1}$: $\nu$NH; 3425, $\nu_{C=O}$; 1670.

m.p. 226.5°–228.5° C. (recrystallized from DMF-isopropanol)

EXAMPLE 13

(1) In 50 ml of toluene were suspended 5 g of 1-(4-aminobenzyl)-4-n-hexyl-2,3-dioxopiperazine and 2.68 g of sodium isothiocyanate, followed by adding dropwise thereto 1.54 ml of trifluoroacetic acid at 80° to 90° C. over a period of 2 hours. After the completion of the addition, the resulting mixture was subjected to reaction under reflux for one hour. After the completion of the reaction, the solvent was removed by decantation, and the oily residue thus obtained was washed with hot water, and then allowed to cool to obtain a solid mass. The solid mass was washed with ethanol, and then filtered to obtain 5 g (83.6% yield) of pale yellow crystals. The crystals were recrystallized from methanol-ethanol to obtain pale yellow crystals of 1-n-hexyl-4-[4-(N-thiocarbamoyl)aminobenzyl]-2,3-dioxopiperazine having a melting point of 197° to 198° C.

IR(KBr)cm$^{-1}$: $\nu_{C=O}$; 1670.

(2) In 10 ml of methanol was suspended 940 mg of 1-n-hexyl-4-[4-(N-thiocarbomyl)aminobenzyl]-2,3-dioxopiperazine, followed by adding thereto 0.17 ml of methyl iodide at room temperature, and the resulting mixture was allowed to stand for 24 hours. Subsequently, the mixture was refluxed for 30 minutes, after which the solvent was removed by distillation under reduced pressure to quantitatively obtain a yellow oily hydroiodide of 1-n-hexyl-4-[4-N-(S-methylisothiocarbamoyl)aminobenzyl]-2,3-dioxopiperazine.

IR(neat)cm$^{-1}$: $\nu_{C=O}$; 1670.

(3) In 35 ml of methanol were dissolved 1.3 g of a hydroiodide of 1-n-hexyl-4-[4-N-(S-methylisothiocarbamoyl)aminobenzyl]-2,3-dioxopiperazine and 0.39 ml of ethylenediamine, and the resulting solution was subjected to reaction under reflux for 24 hours. After the completion of the reaction, the solvent was removed by distillation under reduced pressure, and the residue obtained was dissolved in 35 ml of chloroform, and the extract was then washed successively with 2.5 N aqueous sodium hydroxide solution and water. The chloroform layer was dried over anhydrous magnesium sulfate, after which the solvent was removed by distillation under reduced pressure, and the residue thus obtained was purified by column chromatography (Merk Art. 1076, eluted with chloroform:ethanol=20:1), and then recrystallized from chloroform-ethyl acetate to obtain 500 mg (51.9% yield) of white crystals of 1-n-hexyl-4-[4-(2-imidazolidinyl)aminobenzyl]-2,3-dioxopiperazine having a melting point of 170° to 171° C.

IR(KBr)cm$^{-1}$: $\nu_{NH}$; 3325, $\nu_{C=O}$; 1660.

EXAMPLE 14

In 3 ml of carbon disulfide were dissolved 1.4 g of dicyclohexyl carbodiimide and 2 ml of pyridine, followed by adding dropwise thereto a solution of 2 g of 1-(4-aminobenzyl)-4-n-hexyl-2,3-dioxopiperazine in 10 ml of pyridine at −10° C. over a period of 10 minutes. Subsequently, the resulting mixture was allowed to stand at room temperature for 24 hours. Thereafter, the solvent was removed by distillation under reduced pressure, and 20 ml of benzene was added to the residue. The insoluble matters were removed by filtration and the filtrate was evaporated to dryness under reduced pressure. The residue obtained was purified by column chromatography (Wako gel C-200, eluted with ethyl acetate) and then recrystallized from ethyl acetate-diethyl ether to obtain 1.4 g (61.4% yield) of white crystals of 1-n-hexyl-4-(4-isothiocyanobenzyl)-2,3-dioxopiperazine having a melting point of 145° to 146.5° C.

IR(KBr)cm$^{-1}$: $\nu_{NCS}$; 2100, 2115, 2175, $\nu_{C=O}$; 1650, 1670.

(2) In 10 ml of ethyl acetate was dissolved 460 mg of o-phenylenediamine, followed by adding dropwise thereto a solution of 1.4 g of 1-n-hexyl-4-(4-isothiocyanobenzyl)-2,3-dioxopiperazine in 15 ml of ethyl acetate with stirring at 55° C. over a period of 10 minutes. After the completion of the addition, the resulting mixture was further subjected to reaction with stirring at 65° C. for 30 minutes. After the completion of the reaction, the mixture was allowed to cool, and the crystals precipitated were collected by filtration to contain 1.8 g (98% yield) of white crystals. Recrystallization from ethylene glycol monomethyl ether-ethanol gave white crystals of 1-{4-[N-(2-aminophenyl)thiocarbamoyl]aminobenzyl}-4-n-hexyl-2,3-dioxopiperazine having a melting point of 160° to 160.5° C.

IR(KBr)cm$^{-1}$: $\nu_{C=O}$; 1670.

(3) In 25 ml of DMF was dissolved 1 g of 1-{4-[N-(2-aminophenyl)thiocarbamoyl]aminobenzyl}-4-n-hexyl-2,3-dioxopiperazine, followed by adding thereto 600 mg of yellow mercuric oxide, and the resulting mixture was subjected to reaction with stirring at 60° to 65° C. for one hour. After the completion of the reaction, the inorganic matters were removed by filtration and the solvent in the filtrate was removed by distillation under reduced pressure. The residue thus obtained was recrystallized from methanol to obtain 600 mg (64.6% yield) of brown crystals of 1-[4-(2-benzimidazolyl)aminobenzyl]-4-n-hexyl-2,3-dioxopiperazine having a melting point of 280° to 281° C.

IR(KBr)cm$^{-1}$: $\nu_{C=O}$; 1670.

EXAMPLE 15

(1) A mixture of 1.7 g of 1-benzyl-4-[4-N-(5-ethoxycarbonyl-2-pyrimidinyl)aminobenzyl]-2,3-dioxopiperadine, 4.4 ml of 1 N aqueous sodium hydroxide solution, 30 ml of methanol and 30 ml of water was subjected to reaction under reflux for 30 min. After the completion of the reaction, the reaction mixture was concentrated to a half volume, and then neutralized with 6 N hydrochloric acid. The crystals precipitated were collected by filtration, washed with 20 ml of water, and then recrystallized from dimethyl sulfoxide-methanol, to obtain 1.3 g (81.3% yield) of white crystals of 1-benzyl-4-[4-N-(5-carboxy-2-pyrimidinyl)aminobenzyl]-2,3-dioxopiperazine having a melting point of over 285° C.

IR(KBr)cm$^{-1}$: $\nu_{NH}$; 3280, $\nu_{C=O}$; 1660.

(2) In 50 ml of benzyl alcohol was suspended 2.3 g of 1-benzyl-4-[4-N-(5-carboxy-2-pyrimidinyl)aminobenzyl]-2,3-dioxopiperazine, and to the suspension was added 1.15 ml of triethylamine followed by adding 2.53 ml of diphenylphosphoric acid azide. The resulting mixture was subjected to reaction at 100° to 120° C. for 10 hours. After the completion of the reaction, the reaction mixture was concentrated under reduced pressure, and the residue was dissolved in 100 ml of chloroform, after which the resulting solution was washed successively with 50 ml of water, 50 ml of saturated aqueous sodium hydrogencarbonate and 20 ml of saturated aqueous sodium chloride solution, and then dried over anhydrous sodium sulfate. The solvent was removed by distillation under reduced pressure.

Diisopropyl ether was added to the residual liquid until crystals precipitated, and the crystals were collected by filtration, and recrystallized from dimethylsulfoxide-methanol, to obtain 2.3 g (80.4% yield) of white crystals of 1-benzyl-4-[4-(5-benzyloxycarbonylamino-2-pyrimidinyl)aminobenzyl]-2,3-dioxopiperazine having a melting point of 221° to 222° C.

IR(KBr)cm$^{-1}$: $\nu_{NH}$; 3320, $\nu_{C=O}$; 1720, 1665.

EXAMPLE 16

With 1.2 g of sodium hydride (50% purity) was mixed 50 ml of DMF, and 5 g of 1-n-hexyl-2,3-dioxopiperazine was added thereto with stirring at room temperature over a period of 10 minutes. Subsequently, the resulting mixture was subjected to reaction at 50° to 60° C. for 30 minutes, and 20 ml of a DMF solution containing 4.8 g of p-acetaminobenzyl chloride was added dropwise to the reaction mixture at said temperature over a period of 10 minutes, after which the mixture thus obtained was further subjected to reaction at 90° to 95° C. for 15 minutes, and thereafter the solvent was removed by distillation under reduced pressure. The residue was extracted with 100 ml of ethyl acetate, and the extract was washed with water and then a saturated aqueous sodium chloride solution, and then dried over anhydrous magnesium sulfate, after which the solvent was removed by distillation under reduced pressure. The crystals thus obtained were recrystallized from isopropyl alcohol-diisopropyl ether to obtain 7.5 g (86% yield) of white crystals 1-(4-acetylaminobenzyl)-4-n-hexyl-2,3-dioxopiperazine having a melting point of 178.5° to 179.5° C.

IR(KBr)cm$^{-1}$: $\nu_{C=O}$; 1660.
NMR(CDCl$_3$) ppm values:
0.84 (3H, m, —CH$_3$×1)
1.06–1.74 (8H, CH$_2$×4)
2.16 (3H, —COCH$_3$×1)
3.16–3.56 (6H, >CH$_2$×3)
4.49 (2H, >CH$_2$×1)
6.99 (2H, d, J=9 Hz, benzene ring H×2)
7.39 (2H, J=9 Hz, benzene ring H×2)
8.86 (1H, bs, >NH×1)

Elementary analysis (for C$_{19}$H$_{27}$N$_3$O$_3$); Calcd. (%) C: 66.06; H: 7.88, N: 12.16; Found (%) C: 66.20; H: 7.95, N: 12.03.

EXAMPLE 17

Based on Examples (1) to (16), any starting materials were selected to obtain the compounds shown in Tables 13 to 16.

Note: (1) In Tables 13 to 16, Me=CH$_3$, Et=C$_2$H$_5$, Pr=C$_3$H$_7$, Bu=C$_4$H$_9$, DMF=dimethylformamide, IPA=isopropyl alcohol, IPE=diisopropyl ether, AcOEt=ethyl acetate, MeOH=methanol, EtOH=ethanol, and DMSO=dimethyl sulfoxide.

(2) In the "Process" columns, the ward "Pro." number refers to the process number stated in the description of the specification, and the compound referred to in the line in which the "Pro." number appears was synthesized in the same manner as in the Example mentioned hereinbefore concerning the said process, or according to the method described in the specification based on said Example.

(3) In the "Process" columns, the "Ex." number refers to No. of the Examples mentioned hereinbefore, and the compound mentioned in the line in which the "Ex." number is stated was synthesized in the same manner as in the Example or based on the Example.

(4) In the "Recrystallization Solvent" column, the term "Column" means that the product was purified by a column chromatography.

TABLE 13

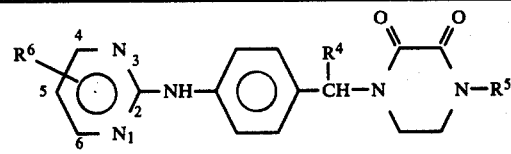

| R$^4$ | R$^5$ | R$^6$ | m.p. (°C.) | Recrystallization Solvent | Process |
|---|---|---|---|---|---|
| H | —CH$_2$—C$_6$H$_4$—COMe | — | 209 | MeOH | Pro. 1 |
| H | —CH$_2$—C$_6$H$_4$—NO$_2$ | — | 214–215 | DMF—IPA | Pro. 1 |
| H | —CH$_2$—C$_6$H$_4$—Cl | — | 216–217 | EtOH—CHCl$_3$ | Pro. 1 |
| H | —CH$_2$—C$_6$H$_4$—NH$_2$ | — | 190–192.5 | EtOH | Ex. 3 |
| H | —CH$_2$—C$_6$H$_4$—NEt$_2$ | — | 131 | EtOH | Pro. 4 |
| H | —CH$_2$—C$_6$H$_3$(MeO)—OMe | — | 186 | MeOH | Pro. 4 |

TABLE 13-continued (XIX)

[Structure: R⁶ substituted pyrimidine ring (positions labeled 4, 5, 6, N₁, 2, N₃) —NH—phenyl—CH(R⁴)—N(cyclic imide with two C=O groups)—N—R⁵]

| R⁴ | R⁵ | R⁶ | m.p. (°C.) | Recrystallization Solvent | Process |
|---|---|---|---|---|---|
| H | —CH₂—phenyl | 5-NH₂ | 166–168 | MeOH—IPE | Ex. 8 |
| H | —CH₂—phenyl | 5-COOEt | 199–200 | IPE—CHCl₃ | Pro. 4 |
| H | -n-C₆H₁₃ | 4-NH₂ | 205–206 | EtOH | Pro. 4 |
| H | —CH(Me)—phenyl | — | 176–177 | MeOH—CHCl₃ | Pro. 1 |
| H | —CH₂—cyclohexyl(H)—COOMe | — | 152.5–154 | AcOEt—IPE | Pro. 1 |
| H | —CH₂CO—phenyl | — | 208.5–209.5 | EtOH—H₂O | Pro. 1 |
| H | —CH₂CH₂—phenyl | — | 184 | IPA | Pro. 1 |
| H | —CH₂CH₂CH₂—phenyl | — | 155–156 | EtOH—CHCl₃ | Pro. 1 |
| H | —CH₂—piperidinyl(H)(N-Me) | — | 138–140 | IPA | Pro. 1 |
| H | pyrazinyl | — | 255 | MeOH—CHCl₃ | Pro. 1 |
| H | —CH₂—pyrazinyl | — | 168–170 | MeOH | Pro. 1 |
| H | —CH₂—furyl—OCOMe | — | 190–191 | MeOH | Pro. 1 |

TABLE 13-continued (XIX)

| R⁴ | R⁵ | R⁶ | m.p. (°C.) | Recrystallization Solvent | Process |
|---|---|---|---|---|---|
| H | —CH₂-(2-pyridyl) | — | 160–161 | MeOH | Pro. 1 |
| H | —CH₂-(6-NHCOMe-2-pyridyl) | — | 199 | MeOH—CHCl₃ | Pro. 1 |
| H | —CH₂-(6-COOMe-3-pyridyl) | — | 193.5 | MeOH—CHCl₃ | Pro. 1 |
| H | —CH₂-phenyl | — | 209–210.5 | IPA | Pro. 4 |
| H | —CH₂-cyclohexyl | — | 188–189 | MeOH | Pro. 1 |

TABLE 14

(XX)

| R⁷ | R⁵ | n | m.p. (°C.) | Recrystallization Solvent | Process |
|---|---|---|---|---|---|
| 3-NH₂, 5-NH₂ | —CH₂-phenyl | 2 | 112–114 | Column | Ex. 11 |
| 5-NH₂, 6-Me | —CH₂-phenyl | 2 | 176–178 | Column | Ex. 11 |
| 4-Me, 5-NH₂ | —CH₂-phenyl | 1 | 160–163 | Column | Ex. 11 |
| 4-Me, 5-NO₂ | —CH₂-phenyl | 2 | 215.5–216 | MeOH | Pro. 4 |

TABLE 14-continued
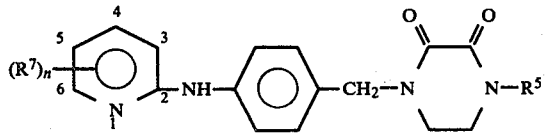
(XX)
| R⁷ | R⁵ | n | m.p. (°C.) | Recrystallization Solvent | Process |
|---|---|---|---|---|---|
| 5-NO₂, 6-Me | 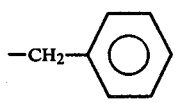 | 2 | 210–212 | DMSO | Pro. 4 |
| 4-Me, 5-NH₂, 6-Me | 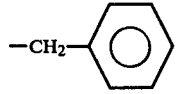 | 3 | 223–224 | MeOH | Ex. 11 |
| 5-OEt | 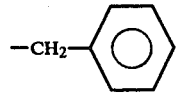 | 1 | 141–142 | AcOEt | Pro. 4 |
| 3-NO₂ | 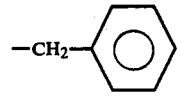 | 1 | 204–205 | DMSO—H₂O | Pro. 4 |
| 3-NO₂, 5-NO₂ | 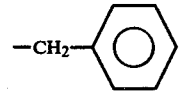 | 2 | 204–206 | DMSO | Pro. 4 |
| 4-Me, 5-NO₂, 6-Me | 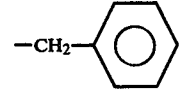 | 3 | 251–253 | DMSO | Pro. 4 |
| 3-NH₂ | 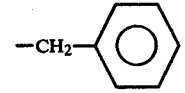 | 1 | 88–89 | Column | Ex. 11 |
| — | 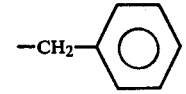 | 0 | 207–209 | MeOH—CHCl₃ | Pro. 4 |
| 5-Me | 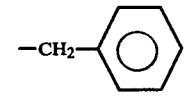 | 1 | 201–202 | EtOH | Pro. 4 |
| 5-Cl | 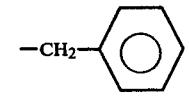 | 1 | 237–238 | EtOH | Pro. 4 |
| — | 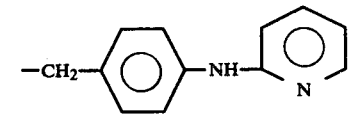 | 0 | 204–207 | DMF—IPA | Ex. 12 |
| — | n-C₆H₁₃ | 0 | 157 | IPA | Pro. 4 |

TABLE 14-continued (XX)

Structure: $(R^7)_n$-pyridine(positions 2,3,4,5,6, N at 1)-NH-phenyl-CH$_2$-N(C=O)(C=O)N-R$^5$ (piperazine-2,3-dione ring)

| R$^7$ | R$^5$ | n | m.p. (°C.) | Recrystallization Solvent | Process |
|---|---|---|---|---|---|
| 5-NH$_2$ | -CH$_2$-phenyl-NH-pyridine-NH$_2$ (5-amino) | 1 | 129–131 | Column | Ex. 11 |
| 5-NO$_2$ | -CH$_2$-phenyl-NH-pyridine-NO$_2$ (5-nitro) | 1 | >300 | DMF | Ex. 12 |

TABLE 15

(XXI)

Structure: R$^1$R$^2$N-phenyl-CH$_2$-N(C=O)(C=O)N-R$^5$

| R$^2$ | R$^1$ | R$^5$ | m.p. (°C.) | Recrystallization Solvent | Process |
|---|---|---|---|---|---|
| H | pyridine-CH$_2$- | -n-C$_6$H$_{13}$ | 177(d) dihydrochloride monohydrate | IPA—H$_2$O | Pro. 4 |
| H | pyridine-CH$_2$- (4-) | -n-C$_6$H$_{13}$ | 159–160 | AcOEt | Pro. 4 |
| H | pyridine-CO- (2-) | -n-C$_6$H$_{13}$ | 148.5–149.5 | IPA | Pro. 4 |
| H | ClCH$_2$CO— | -n-C$_6$H$_{13}$ | 179 | MeOH | Pro. 4 |
| H | FCH$_2$CO— | -n-C$_6$H$_{13}$ | 147–149 | IPA | Pro. 4 |
| H | ClCH$_2$CH$_2$CO— | -n-C$_6$H$_{13}$ | 173–175 | MeOH | Pro. 4 |
| H | Ac | -n-C$_6$H$_{13}$ | 178.5–179.5 | IPA—IPE | Pro. 4 |
| H | Et | -n-C$_6$H$_{13}$ | 109–110.5 | AcOEt—IPE | Pro. 4 |
| H | iso-Pr | -n-C$_6$H$_{13}$ | 116–117 | AcOEt—IPE | Pro. 4 |
| n-Bu | n-Bu | -n-C$_6$H$_{13}$ | 170–172 hydrochloride | EtOH—Et$_2$O | Pro. 1 |
| Me | Me | -n-C$_6$H$_{13}$ | 109–110 | AcOEt—IPE | Pro. 1 |
| Et | Ac | -n-C$_6$H$_{13}$ | 101.5–103.5 | AcOEt—IPE | Pro. 5 |
| Ac | Ac | -n-C$_6$H$_{13}$ | Oil IR (neat)cm$^{-1}$: $\nu_{C=O}$ 1690 | Column | Pro. 5 |
| Et | ClCH$_2$CO— | -n-C$_6$H$_{13}$ | Oil IR (neat)cm$^{-1}$: $\nu_{C=O}$ 1665, 1675 | Column | Pro. 5 |
| ClCH$_2$CH$_2$— | ClCH$_2$CH$_2$— | -n-C$_6$H$_{13}$ | Oil IR (neat)cm$^{-1}$: $\nu_{C=O}$ 1697, 1668 | Column | Pro. 5 |

TABLE 15-continued

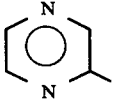
(XXI)

| R² | R¹ | R⁵ | m.p. (°C.) | Recrystallization Solvent | Process |
|---|---|---|---|---|---|
| H | 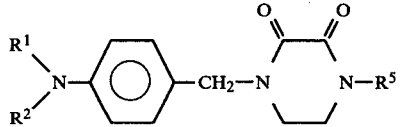 | -n-C₆H₁₃ | 180–181 | IPA | Pro. 4 |
| 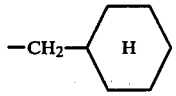 | | | 148 | EtOH—CHCl₃ | Pro. 7 |
| Et | Et | —(CH₂)₆Br | 75.5–75.7 | AcOET—IPE | Pro. 1 |
| Et | Et | —(CH₂)₂O—n-Bu | 59–61 | Et₂O—Petroleum ether | Pro. 1 |
| Et | Et | —CH₂CHEt₂ | 105–106 | AcOET—IPE | Pro. 1 |
| Et | Et | —CH₂CH=CH—CH=CH—Me | Oil IR (neat)cm⁻¹: $\nu_{C=O}$ 1670 | Column | Pro. 1 |
| Et | Et | —H | 214.5–215.5 | EtOH | Pro. 2 |
| Et | Et | -n-C₆H₁₃ | 194–195 hydrochloride | EtOH | Pro. 1 |
| Et | Et | 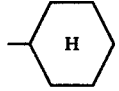 | 109 | AcOEt | Pro. 1 |
| Et | Et | 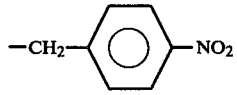 | 159–161 | AcOEt | Pro. 1 |
| Et | Et | 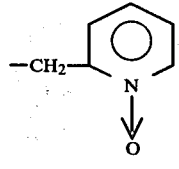 | 223 | EtOH—CHCl₃ | Pro. 7 |
| Et | Et | —CH₂CH₂NH₂ | 225–226 dihydrochloride | EtOH—IPE | Pro. 1 |
| Et | Et | —CH₂CH₂Cl | 125–126 | IPA | Pro. 1 |
| Et | Et | 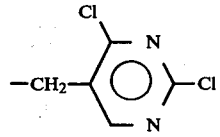 | 113 | AcOEt | Pro. 1 |
| Et | Et | 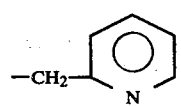 | 161.5–162 | EtOH | Pro. 1 |
| Et | Et |  | 95 | AcOEt—IPE | Pro. 1 |

TABLE 15-continued

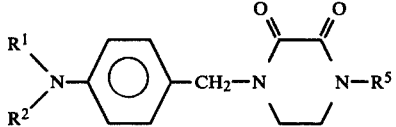
(XXI)

| R² | R¹ | R⁵ | m.p. (°C.) | Recrystallization Solvent | Process |
|---|---|---|---|---|---|
| Et | Et | 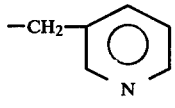 —CH₂— (3-pyridyl) | 150–152 | IPA | Pro. 1 |
| Et | Et |  (pyrazine) | 153 | EtOH | Pro. 1 |
| Et | Et | 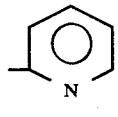 (pyridyl) | 165–166 | EtOH | Pro. 1 |
| Et | Et | 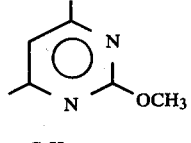 (2,4-dimethoxypyrimidinyl) | 160–161 | EtOH | Pro. 1 |
| H | 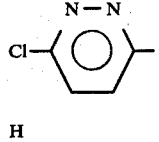 (6-chloro-3-pyridazinyl) | -n-C₆H₁₃ | 267–268 | EtOH | Pro. 4 |
| H | H | 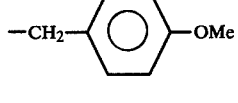 —CH₂-(2,4-dimethoxyphenyl) | 196–199 | MeOH—CHCl₃ | Pro. 7 |
| H | H | 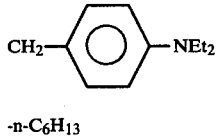 —CH₂—C₆H₄—NEt₂ | 130 | IPA | Pro. 7 |
| H | 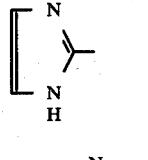 (imidazolyl) | -n-C₆H₁₃ | 146–147 | AcOEt—CHCl₃ | Pro. 6 |
| H | 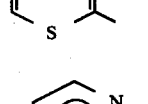 (thiazolyl) | -n-C₆H₁₃ | 221 | EtOH | Pro. 4 |
| H | 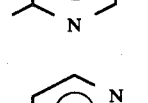 (pyrimidinyl) | -n-C₆H₁₃ | 148 | EtOH | Pro. 4 |
| H | 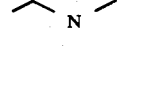 (pyrimidinyl) | —CH₂—C₆H₅ | 206–207 | EtOH | Pro. 4 |

TABLE 15-continued (XXI)

[Structure: R¹R²N–C₆H₄–CH₂–N(ring with two C=O)–N–R⁵]

| R² | R¹ | R⁵ | m.p. (°C.) | Recrystallization Solvent | Process |
|---|---|---|---|---|---|
| CH₂(CH₂CH₂)(CH₂CH₂) (piperidinyl) | | -n-C₆H₁₃ | 234–236 hydrochloride | IPA | Pro. 1 |
| CH=CH–CH=CH (pyrrolyl) | | -n-C₆H₁₃ | 185 | MeOH | Pro. 1 |

TABLE 16

(XXII)

[Structure with R₁R₂N– on position 4, R₃ on ring, –CH₂–N(dioxopiperazine)–N–n-C₆H₁₃]

| R₁ | R₂ | R₃ | m.p. (°C.) | Recrystallization Solvent | Process |
|---|---|---|---|---|---|
| H | H | 3-Me | 170 | IPA | Pro. 7 |
| Et | Et | 2-Cl | 92–93 | EtOAc—IPE | Pro. 4 |
| Et | Et | 3-Cl | 62–63 | EtOAc—IPE | Pro. 5 |
| Et | Et | 3-Me | Oil IR(neat)cm⁻¹: $v_{C=O}$ 1665 | Column | Pro. 5 |
| Et | Et | 3-Br | 176 hydrochloride | IPA—IPE | Pro. 1 |
| Et | Et | 2-NEt₂ | Oil IR(neat)cm⁻¹: $v_{C=O}$ 1650 | Column | Pro. 1 |

What is claimed is:

1. A compound represented by the formula

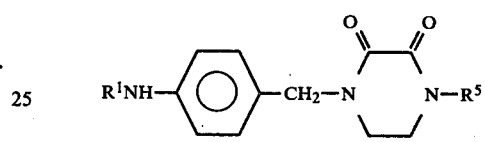

wherein $R^1$ represents 2-thiazolyl, 4-thiazolyl or 5-thiazolyl; $R^5$ represents $C_{1-8}$ alkyl; or a pharmaceutically acceptable acid addition salt thereof.

2. The compound 1-n-hexyl-4-[4-(2-thiazolyl-amino)-benzyl]-2,3-dioxopiperazine of the formula:

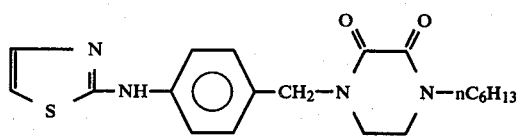

or a pharmaceutically acceptable acid addition salt thereof.

* * * * *